US010278382B2

(12) United States Patent
Wynalda, Jr.

(10) Patent No.: US 10,278,382 B2
(45) Date of Patent: May 7, 2019

(54) DEVICE FOR CREATING AND DISTRIBUTING VAPORIZED SCENT

(71) Applicant: Fourth Arrow, LLC, Comstock Park, MI (US)

(72) Inventor: Robert M. Wynalda, Jr., Comstock Park, MI (US)

(73) Assignee: Wyndscent, LLC, Belmont, MI (US)

( * ) Notice: Subject to any disclaimer, the term of this patent is extended or adjusted under 35 U.S.C. 154(b) by 37 days.

(21) Appl. No.: 15/452,318

(22) Filed: Mar. 7, 2017

(65) Prior Publication Data

US 2017/0238527 A1 Aug. 24, 2017

Related U.S. Application Data

(63) Continuation-in-part of application No. 15/137,677, filed on Apr. 25, 2016, now Pat. No. 9,585,981, which is a continuation-in-part of application No. 14/941,428, filed on Nov. 13, 2015, now Pat. No. 9,426,977.

(Continued)

(51) Int. Cl.
*A01M 13/00* (2006.01)
*A01M 1/20* (2006.01)
*A61L 9/03* (2006.01)
*A61L 9/12* (2006.01)
*F01K 5/00* (2006.01)
*F22B 1/28* (2006.01)
*H05B 3/00* (2006.01)
*A01M 29/12* (2011.01)

(Continued)

(52) U.S. Cl.
CPC ........ *A01M 31/008* (2013.01); *A01M 1/2072* (2013.01); *A01M 1/2077* (2013.01); *A01M 29/12* (2013.01); *A61L 9/032* (2013.01); *A61L 9/037* (2013.01); *A61L 9/12* (2013.01); *F01K 5/00* (2013.01); *F22B 1/284* (2013.01); *H05B 3/0014* (2013.01); *A61L 9/013* (2013.01); *A61L 2209/111* (2013.01); *A61L 2209/133* (2013.01); *A61L 2209/134* (2013.01); *A61L 2209/135* (2013.01); *A61L 2209/15* (2013.01)

(58) Field of Classification Search
None
See application file for complete search history.

(56) References Cited

U.S. PATENT DOCUMENTS 1,771,366 A  10/1926 Wyss et al.
1,819,123 A   5/1927 Robinson
(Continued)

FOREIGN PATENT DOCUMENTS

DE  19625486 A1  1/1998

*Primary Examiner* — Thor S Campbell
(74) *Attorney, Agent, or Firm* — Zollinger & Burleson Ltd.

(57) ABSTRACT

A scent vaporizing and distribution device uses an electric heating element to rapidly vaporize a liquid scent material. An airflow generator is used to create a distribution airflow that distributes the vapor from the device. The airflow generator can be an electric-powered fan or a manually-powered pump or squeezable bladder. The liquid scent material can include a glycol or a water-glycol mixture. A scent material such as liquid or powdered deer urine or a pleasant scent that can be used as a room or automobile or room freshener is mixed with the liquid. The vapor generator can be removable and replaceable such that different scents can be used with a single airflow generator or an empty generator can be replaced.

29 Claims, 23 Drawing Sheets

Related U.S. Application Data

(60) Provisional application No. 62/163,603, filed on May 19, 2015, provisional application No. 62/156,023, filed on May 1, 2015, provisional application No. 62/151,989, filed on Apr. 23, 2015.

(51) Int. Cl.
    *A01M 31/00*      (2006.01)
    *A61L 9/013*      (2006.01)

(56) References Cited

U.S. PATENT DOCUMENTS

| | | | |
|---|---|---|---|
| 1,944,108 | A | 10/1928 | Robinson |
| 2,254,680 | A | 8/1938 | Harvey |
| 2,311,199 | A | 2/1943 | Astradsson |
| 2,882,240 | A | 2/1956 | Charwat |
| 3,658,719 | A | 4/1972 | McConnaughey |
| 3,990,987 | A | 11/1976 | Rogers |
| 3,993,444 | A | 11/1976 | Brown |
| 4,146,566 | A | 3/1979 | Gaiser |
| 4,166,087 | A | 8/1979 | Cline et al. |
| 4,306,679 | A | 12/1981 | Dusek et al. |
| 4,327,056 | A | 4/1982 | Gaiser |
| 4,346,059 | A | 8/1982 | Spector |
| 4,423,626 | A | 1/1984 | Herschede |
| 4,813,437 | A | 3/1989 | Ray |
| 4,869,407 | A | 9/1989 | Booth, Jr. et al. |
| 4,922,901 | A | 5/1990 | Brooks et al. |
| 4,953,763 | A | 9/1990 | Kierum et al. |
| 5,094,024 | A | 3/1992 | Duke |
| 5,117,821 | A | 6/1992 | White |
| 5,186,118 | A | 2/1993 | Stinson |
| 5,261,424 | A | 11/1993 | Sprinkel, Jr. |
| 5,388,762 | A | 2/1995 | Bryson, Sr. |
| 5,894,841 | A | 4/1999 | Voges |
| 5,901,490 | A | 5/1999 | Lush |
| 5,914,119 | A | 6/1999 | Dawson |
| 6,254,836 | B1 | 7/2001 | Fry |
| 6,421,502 | B1 | 7/2002 | Aronie et al. |
| 6,857,214 | B1 | 2/2005 | Pelissier |
| 7,290,445 | B2 | 11/2007 | Kirollos et al. |
| 7,350,411 | B2 | 4/2008 | Anderson |
| 7,377,493 | B2 | 5/2008 | Thomas |
| 7,682,575 | B2 | 3/2010 | Hurwitz et al. |
| 7,721,597 | B2 | 5/2010 | Onishi |
| 7,765,863 | B1 | 8/2010 | Woolsey |
| 7,874,207 | B2 | 1/2011 | Galley et al. |
| 7,883,677 | B2 | 2/2011 | Palozzi |
| 8,422,869 | B2 | 4/2013 | Joseph |
| 8,424,379 | B2 | 4/2013 | Bibby |
| 8,903,228 | B2 | 12/2014 | Goodman et al. |
| 9,078,474 | B2 | 7/2015 | Thompson |
| 9,426,977 | B1 | 8/2016 | Wynalda, Jr. |
| 9,532,597 | B2 | 1/2017 | Tucker et al. |
| 9,603,387 | B2 | 3/2017 | Liu |
| 9,739,796 | B2 | 8/2017 | Ferrara, Jr. |
| 2002/0071664 | A1 | 6/2002 | Aronie et al. |
| 2003/0020185 | A1 | 1/2003 | Cox |
| 2005/0016550 | A1 | 1/2005 | Katase |
| 2006/0042373 | A1 | 3/2006 | Kirollos et al. |
| 2008/0098952 | A1 | 5/2008 | Healy et al. |
| 2008/0149665 | A1 | 6/2008 | Hafer et al. |
| 2009/0147506 | A1 | 6/2009 | Robinson |
| 2009/0260271 | A1 | 10/2009 | Bailey |
| 2010/0224119 | A1 | 9/2010 | Morris |
| 2011/0120482 | A1 | 5/2011 | Brenneise |
| 2011/0142429 | A1 | 6/2011 | Joseph |
| 2011/0226236 | A1 | 9/2011 | Buchberger |
| 2012/0204889 | A1 | 8/2012 | Xiu |
| 2012/0230659 | A1 | 9/2012 | Goodman et al. |
| 2013/0213418 | A1 | 8/2013 | Tucker et al. |
| 2013/0220315 | A1 | 8/2013 | Conley et al. |
| 2013/0240638 | A1 | 9/2013 | Kaplan et al. |
| 2014/0276177 | A1 | 9/2014 | Brambilla et al. |
| 2015/0027456 | A1 | 1/2015 | Janardhan et al. |
| 2015/0181944 | A1 | 7/2015 | Li et al. |
| 2015/0296884 | A1 | 10/2015 | Liu |
| 2015/0374039 | A1 | 12/2015 | Zhu |
| 2016/0309701 | A1 | 10/2016 | DeHaven |
| 2016/0310624 | A1 | 10/2016 | Wynalda, Jr. |
| 2016/0339461 | A1 | 11/2016 | Kaplan et al. |

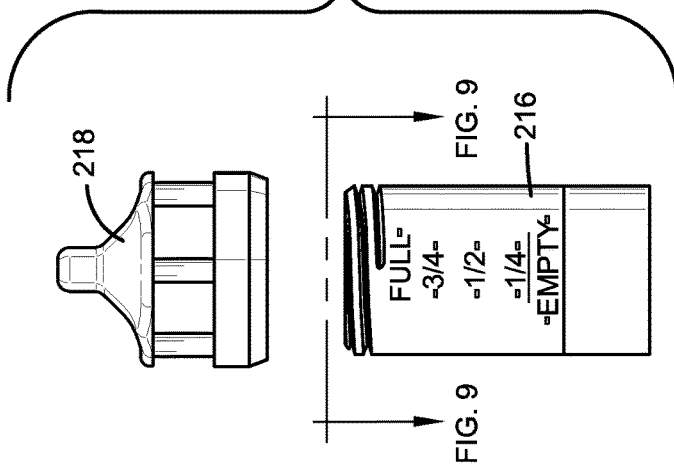
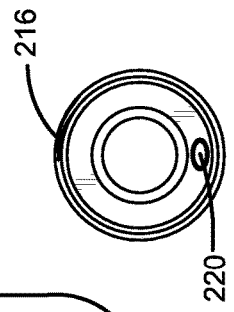
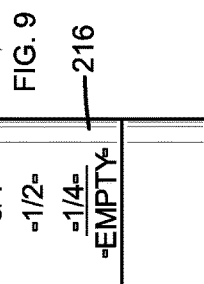
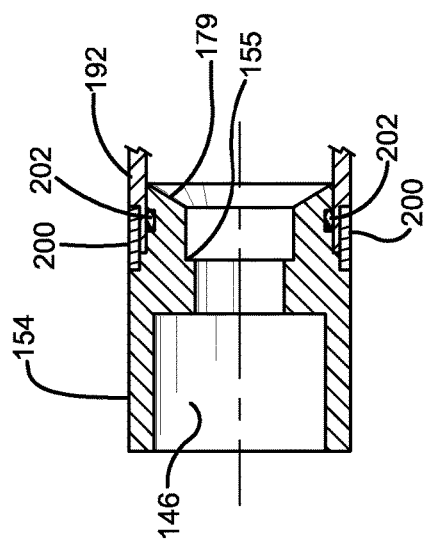
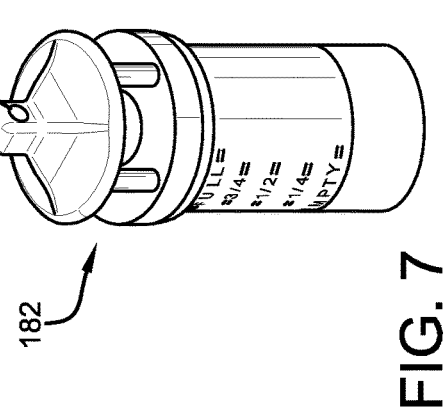

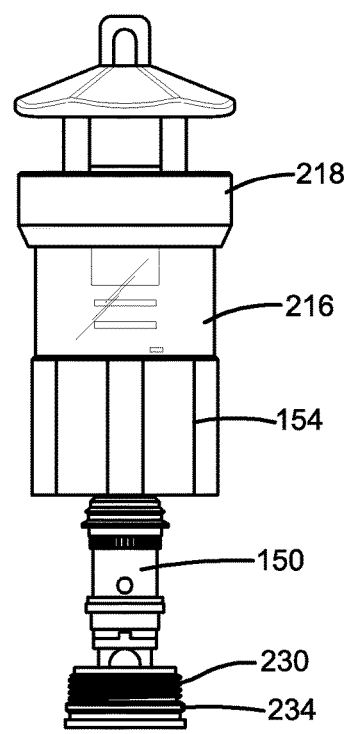
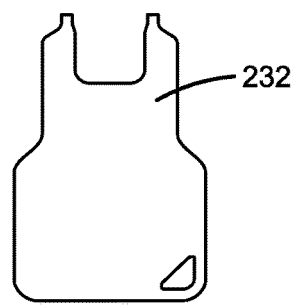
FIG. 16
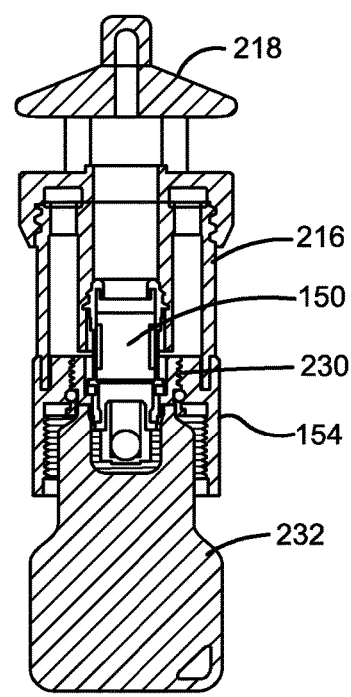
FIG. 17

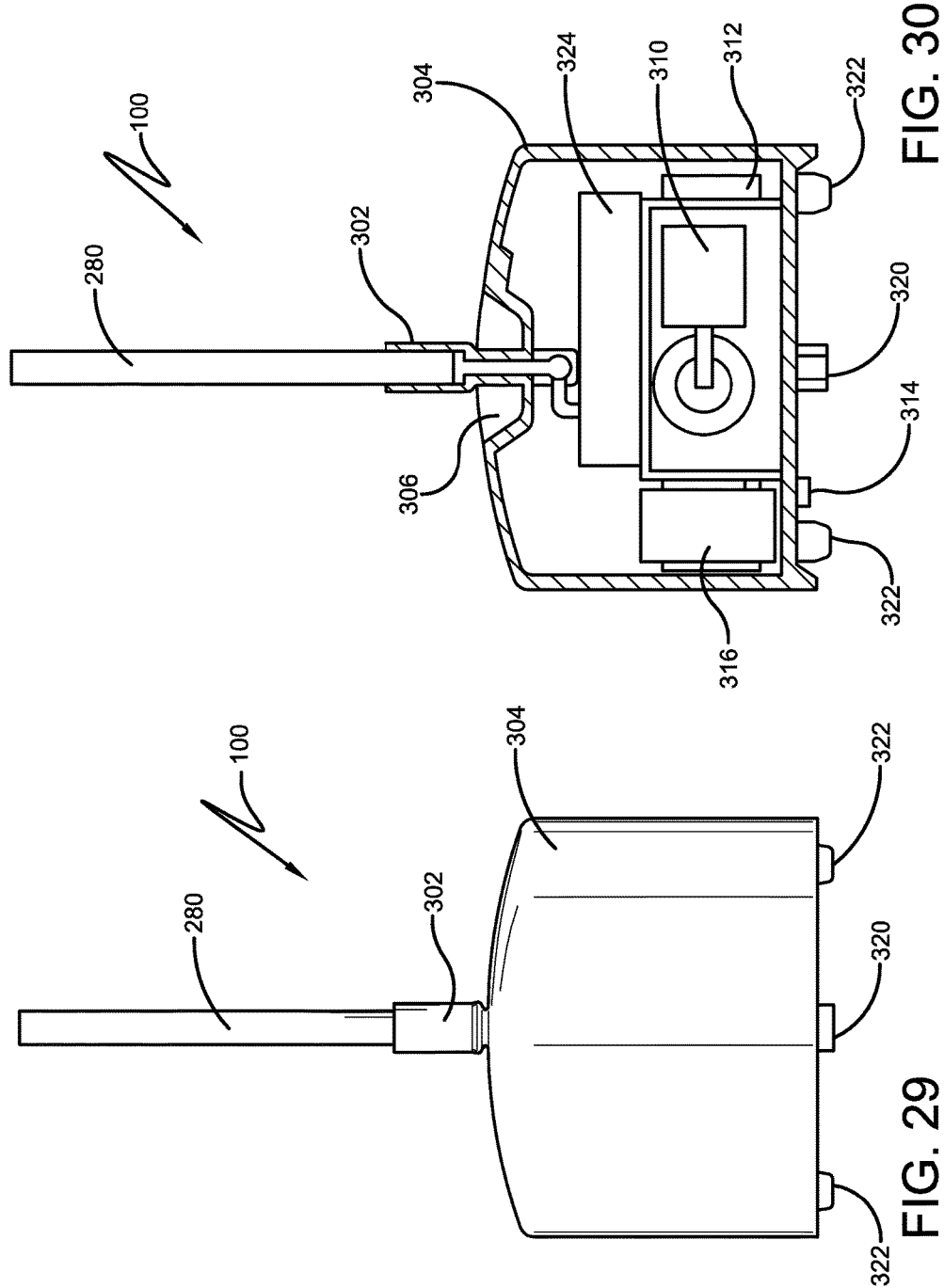

DEVICE FOR CREATING AND DISTRIBUTING VAPORIZED SCENT

CROSS REFERENCE TO RELATED APPLICATIONS

This application is a continuation-in-part application claiming priority to U.S. Pat. No. 9,585,981 which is a continuation-in-part of U.S. Pat. No. 9,426,977; and which claims the benefit of U.S. Provisional Patent Application Ser. No. 62/151,989 filed Apr. 23, 2015; 62/156,023 filed May 1, 2015; 62/163,603 filed May 19, 2015; 62/266,391 filed Dec. 11, 2015; 62/275,559 filed Jan. 6, 2016; 62/276,121 filed Jan. 7, 2016; 62/286,221 filed Jan. 22, 2016; 62/290,743 filed Feb. 3, 2016; 62/298,913 filed Feb. 23, 2016; the disclosures of each are incorporated herein by reference.

BACKGROUND OF THE DISCLOSURE

1. Technical Field

The disclosure generally relates to vaporizing devices used to make and distribute airborne scents such as those used to add a scent to the air in a room or an automobile, distribute an insect repellant, or as aromatic hunting lures, repellants, scent eliminators, or scent covers. More particularly, the disclosure relates to an electric vaporizing device that vaporizes liquid aromatic compositions and distributes the vaporized scents to the atmosphere surrounding the device. Specifically, the disclosure relates to an electric vaporizer configured to vaporize a liquid scent material upon exposure to a heating coil wherein the resulting vapor is distributed with air flow from an airflow generator.

2. Description of the Prior Art

Aromatic materials have long been used by hunters to lure or attract game animals toward a position within range of the hunter. Examples of aromatic materials include doe urine and sweet smelling items such as apple and corn. In some cases, a hunter spreads the smell of a buck in order to lure a different buck seeking to defend territory. Other urines and gland secretions are also used as well as naturally occurring smells from trees and bushes favored by game.

In certain instances, deer hunters, utilizing the aforementioned liquid urine, hunt near scrape marks which have been formed in the ground by the hooves of the deer crossing the territory. Deer scrape the ground to provide a location for defecation or urination, and consequently other deer are attracted to the odors emanating from previously formed scrapes. As a consequence, it is advantageous for hunters to distribute quantities of urine near the previously formed scrapes. A few drops of the liquid urine may be sprinkled in each of the scrapes within range, and in addition a bottle or vial containing some of the liquid urine may be left open on the ground, so that a portion of the liquid urine evaporates into the air to further distribute the aroma.

Unfortunately, individuals hunting in freezing conditions have found that the urine freezes after a certain time in the field, rendering the relatively expensive product useless. In addition, containers or vials which are left on the ground for vaporization of the liquid urine occasionally tip due to the influence of wind and spill the expensive liquid contents onto the earth. Another problem is that a liquid aromatic material has a strong scent immediately after being distributed which then tapers off over time. Hunters design a way to re-strengthen the scent without leaving a blind or stand position.

One solution to the problem of freezing lure is disclosed in U.S. Pat. No. 3,046,192 which uses a hand warmer to warm the lure. Other devices use a burning fuel to warm the material in order to increase the rate of evaporation. One device uses an electrically-power heater disposed within a wick to warm material drawn to the heater.

Other uses for scents during hunting include cover scents and scents that repel game. Repelling scents can be used to prevent game from entering or leaving an area. Other situations where one desires to distribute a scent include freshening the air in a room or inside an automobile. Some scents are used to ward off insects such as citronella used for mosquitos.

SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The disclosure provides a vaporizing and distribution device that uses an electric heating element to rapidly vaporize a scent material that is provided as a liquid to the heating element. The scent material can include a propylene glycol (PG), a vegetable glycerin (VG), a combination of PG and VG, or a combination of PG or VG and water. These substances are mixed with an aromatic material that can be added as a solid or a liquid. The aromatic material can be a hunting lure or a material having a smell that is pleasant to humans or a material that repels animals or insects. The solid aromatic material can be a dehydrated material such as dehydrated animal or game urine such as a deer urine, elk urine, bear urine, or other dehydrated glandular secretions. The liquid aromatic material can be the liquid forms of these materials or scented oils. The scent material is a combination of dehydrated powders, oils created from the distilling of natural ingredients or a combination of both. The powder, oil or combination of the two are combined with propylene glycol or vegetable glycerin. The scent is used for: attractant scent for hunting, cover scent for hunting, pleasant smelling scent, or repellant scent. The disclosure also provides a vaporizable material that eliminates or substantially reduces the user's scent. In an exemplary configuration, the vaporizable material includes an activated carbon mixed with glycol or a mixture of glycol and water.

Another aspect of the disclosure is a vaporizable material that repels game and a method of using the repellant to influence the movement of the game. The repellant material can include the scent of a predator, soap, humans, dogs, and the like. The user can set a scent fence line of vaporizing devices timed to form and distribute the vaporized scent at periodic times. This creates a scent barrier than helps keep game from passing through the area.

Another aspect of the disclosure is a vaporizable material and method of using a vaporizable material for scent elimination. The disclosure provides a vaporizable mixture that includes a percentage of carbon, charcoal, activated carbon, or coconut shell activated carbon, or palm kernel shell charcoal or a combination of these substances. The combination of these substances with a vaporizable material such as the glycol materials discussed above allow a scent elimination substance to be generated to be used by a hunter to eliminate or reduce scents that can alert game to the hunter's presence.

The disclosure provides a vaporizing and distribution device configured to selectively receive disposable cartridges that hold the scent material. In one configuration, the cartridge includes the liquid scent material without a heating element. In another configuration, the cartridge includes the electric heating element as well as the liquid scent material. In any of these configurations, the cartridge can be single use or refillable. In any of these configurations, the cartridge can hold the liquid scent material disposed around a centrally-disposed distribution outlet that directs vapor to a distributor that allows the vapor to be distributed around the entire perimeter of the device.

The disclosure provides a configuration of the device that uses liquid tank and a seal that is used to seal off the liquid tank when the device is not in use.

The disclosure provides scent material composition that includes a base that is readily vaporized by an electric resistive heater and an animal lure aromatic material which can be a dehydrated urine or an animal material such as gland secretions that attract game. Deer urine is provided as an example. The aromatic material also can be a pleasant-smelling material such as a fruit-based material, a flower-based material, or another pleasant-smelling plant or item such that the device may be used for an alternative purpose of freshening air in a room or the air in an automobile. These scents also may be used to cover the scents humans leave while entering or exiting hunting grounds. In one configuration, the user of the scent material mixes the liquid scent material immediately prior to adding it to a vaporizing device in order to provide a fresh liquid scent material. In this configuration, the components of the liquid scent material are provided in separate containers such as one with the scent components (dehydrated urine or glandular secretion materials or other dry scent materials as described above or a scent oil) and the other being the vaporizable liquid (PG, VG, combination or PG and VG, or combination of these with water). The user mixes the two and agitates until the scent material is dissolved into a vaporizable liquid scent that is fresh when added to the vaporizing device. These can be provided in separate bottles or separate chambers of a container that can be mixed on demand by removing a barrier.

The disclosure provides a vaporizer that includes an airflow generator that creates an air flow used to distribute the vapor from the device. The airflow generator can be a fan, a compressed gas cartridge, an air pump, or a device that is collapsed by the user to generate the airflow. The airflow generator can be controlled to provide different airflow speeds. Different embodiments and mounting configurations are provided. In one configuration, the fan is mounted about an axis of rotation that is substantially perpendicular to the longitudinal axis of the device. In another configuration, the axis of rotation for the fan is parallel to the longitudinal dimension of the device. In this second configuration, a magnetic mount is provided. Compressed gas canisters can be used and hand-squeezable bladders can be used. An air pump having a movable bellows can be used to generate the airflow.

The disclosure provides configurations with an electric vaporizer that is selectively connectable to an air bladder that provides the airflow for distributing vapor created by the vaporizer. The devices can use the airflow created by the bladder to activate the vaporizer to create the vapor that is then distributed from the vaporizer by the airflow.

The disclosure provides a vaporizer with a removable power source and a removable power source housing.

The disclosure provides a vapor distribution device having a timer and/or a controller chip that allows the distribution of the hunting lure at selected intervals based on time, temperature, or climate conditions. In one configuration, the user can program the timer and/or controller chip or change the settings of the controller chip in order to change the operation of the device. Another configuration allows the device to be controlled by a remote control such as a mobile computing device such as a mobile smart phone with WIFI, Bluetooth, radio frequency, or cellular communications protocols.

The disclosure also provides a non-programmable hunting lure distribution device which has a fixed distribution timing and volume pattern. This may be combined with a manual trigger to allow for manual operation of the device.

The disclosure provides a vaporizing device having a power supply that is selectively connectable to the vaporizing device and other devices such as a flashlight, an electric device charger, a power adapter for a cell phone, or other devices operable from battery power.

The preceding non-limiting aspects, as well as others, are more particularly described below. A more complete understanding of the processes and the structures of the vaporizing device can be obtained by reference to the accompanying drawings, which are not intended to indicate relative size and dimensions of the assemblies or components thereof. In those drawings and the description below, like numeric designations refer to components of like function. Specific terms used in that description are intended to refer only to the particular structure of the embodiments selected for illustration in the drawings, and are not intended to define or limit the scope of the disclosure.

BRIEF DESCRIPTION OF THE DRAWINGS

FIG. 1 is a rear perspective view of an exemplary configuration of the vaporizing device.

FIG. 2 is a front perspective view of the configuration of the vaporizing device depicted in FIG. 1.

FIG. 3 is a front perspective view of another configuration of the vaporizing device used with a stand.

FIG. 4 is an exploded perspective view of the FIG. 3 configuration.

FIG. 5 is a section view of the FIG. 3 configuration.

FIG. 6 is a section view of the burner holder.

FIG. 7 is a front perspective view of an alternative end cap.

FIG. 8 is an exploded view of the alternative end cap showing the pieces disassembled for refilling.

FIG. 9 is a view taken along line 9-9 of FIG. 8 showing the refill opening.

FIG. 10 is a front elevation view of another configuration of the vaporizing device.

FIG. 11 is a rear elevation view of the configuration of the vaporizing device depicted in FIG. 10.

FIG. 12 is an exploded view of the FIG. 10 configuration.

FIG. 13 is a section view of the FIG. 10 configuration.

FIG. 14 is a perspective view of a sealing cap.

FIG. 15 is a section view showing the sealing cap fully inserted.

FIG. 16 is an exploded view showing a key used to install and remove the burner.

FIG. 17 is a section view showing the burner installed with the key.

FIG. 18 is an exploded view of an alternative fan configuration.

FIG. 19 is a view of an exemplary configuration with a hand-powered squeeze-type airflow generator.

FIG. 29 depicts another configuration of a device for creating and distributing vapor.

FIG. 30 is section view of the device of FIG. 29.

Similar numbers refer to similar parts through the specification.

DETAILED DESCRIPTION OF THE DISCLOSURE

Figure 1:
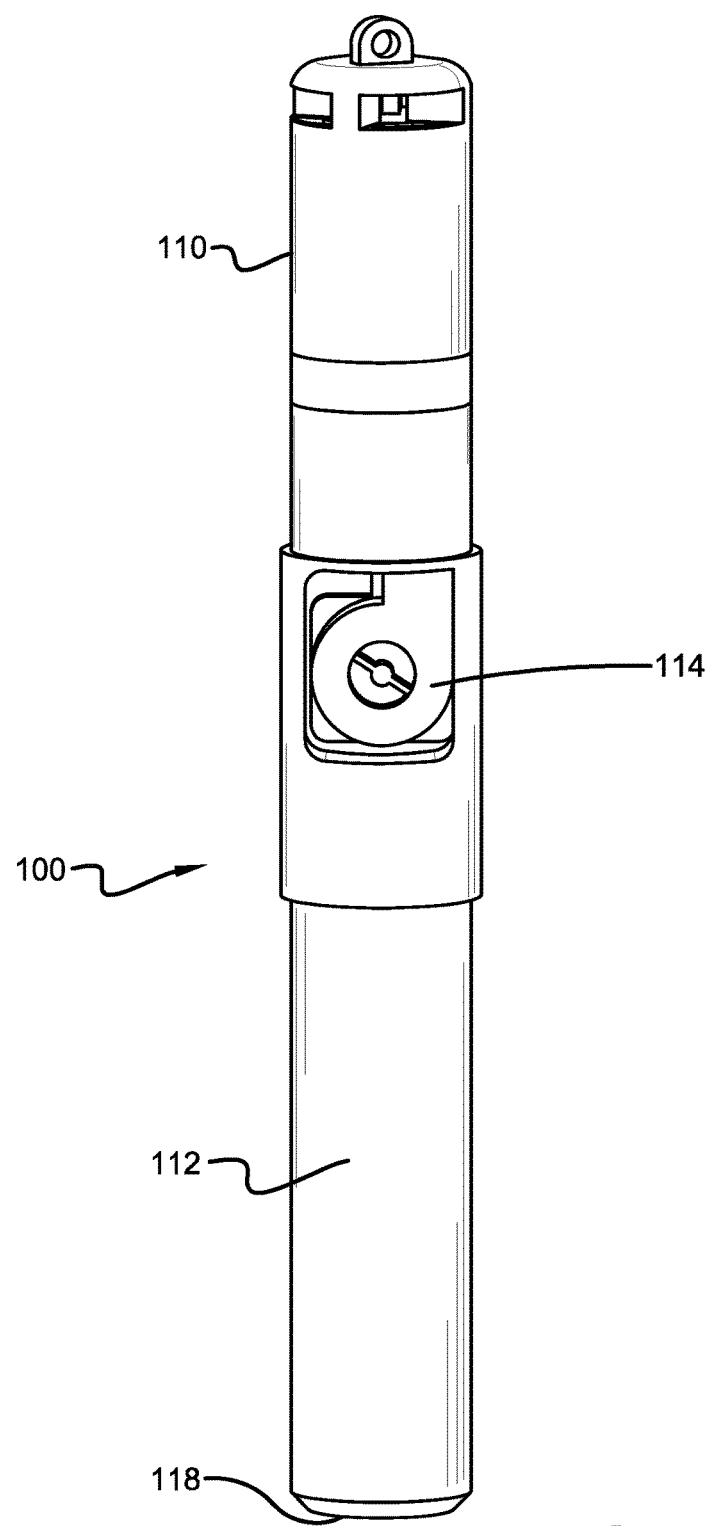
Figure 2:
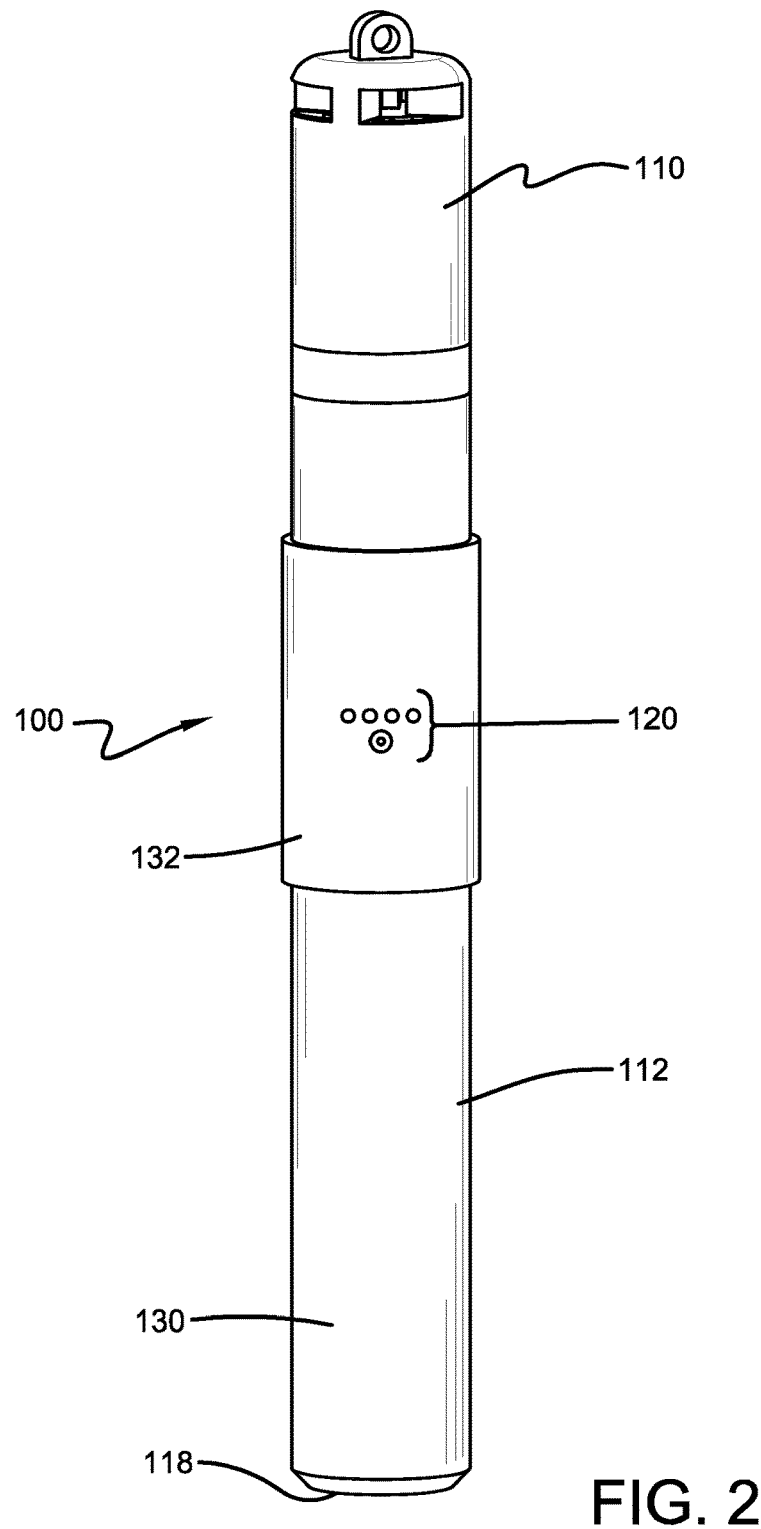
Figure 3:
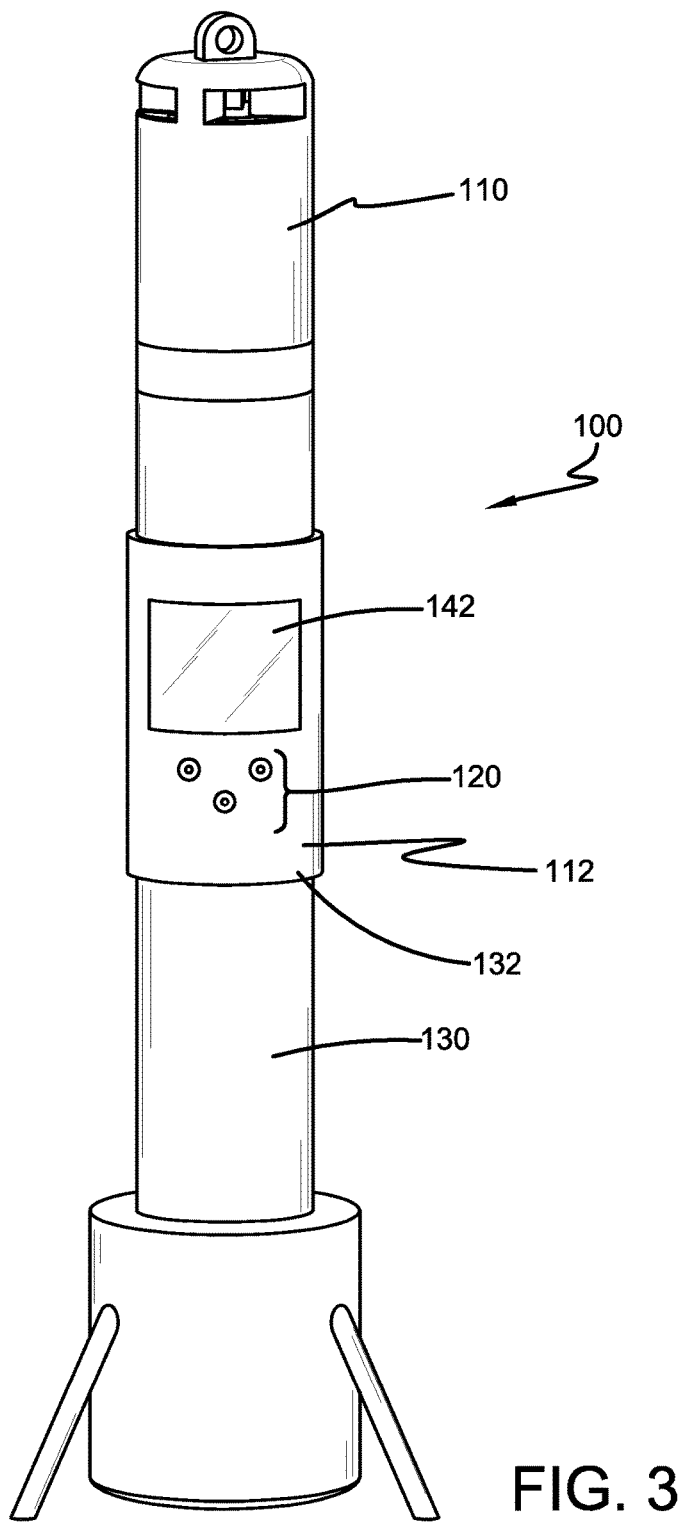
Figure 4:
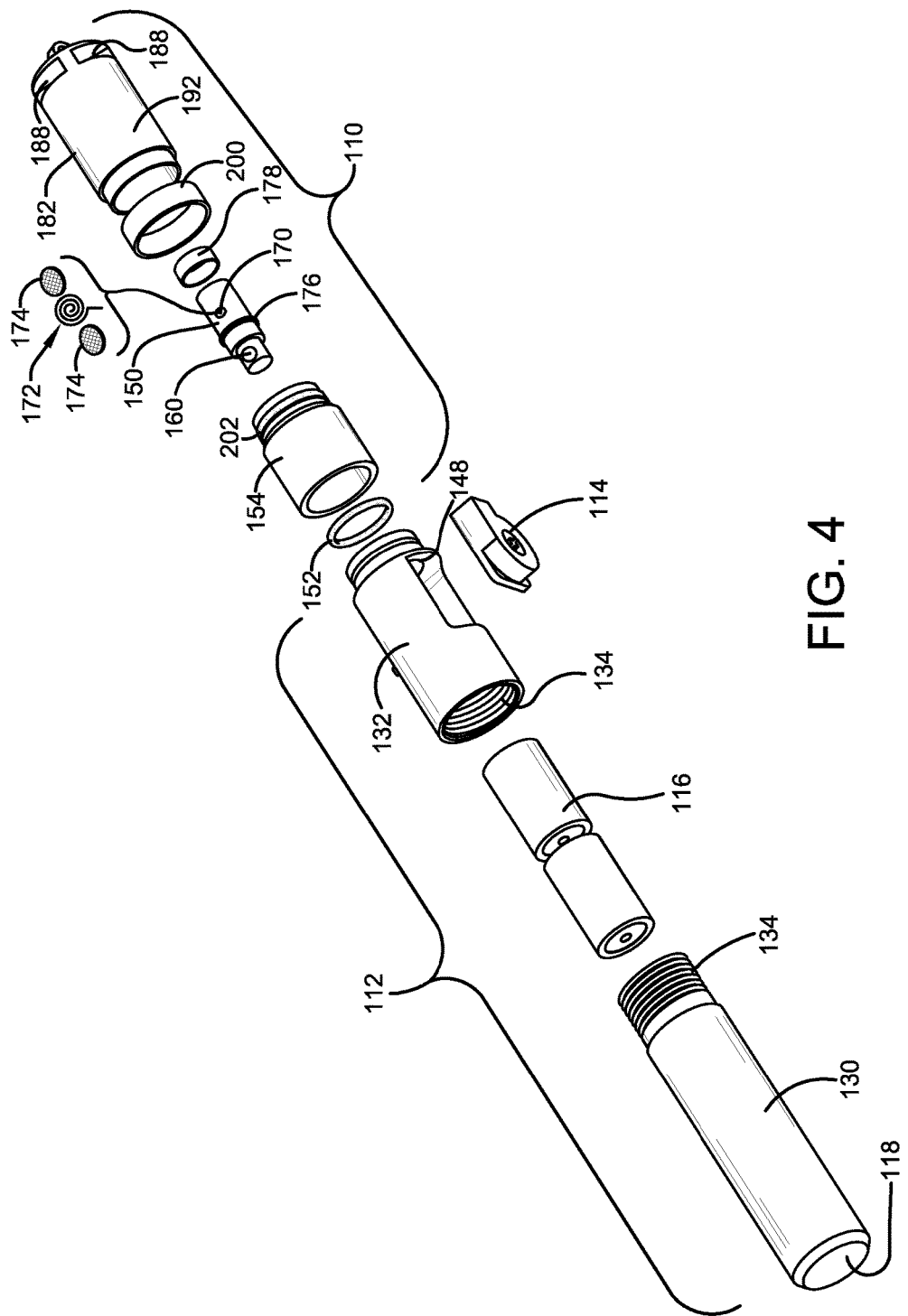
Figure 5:
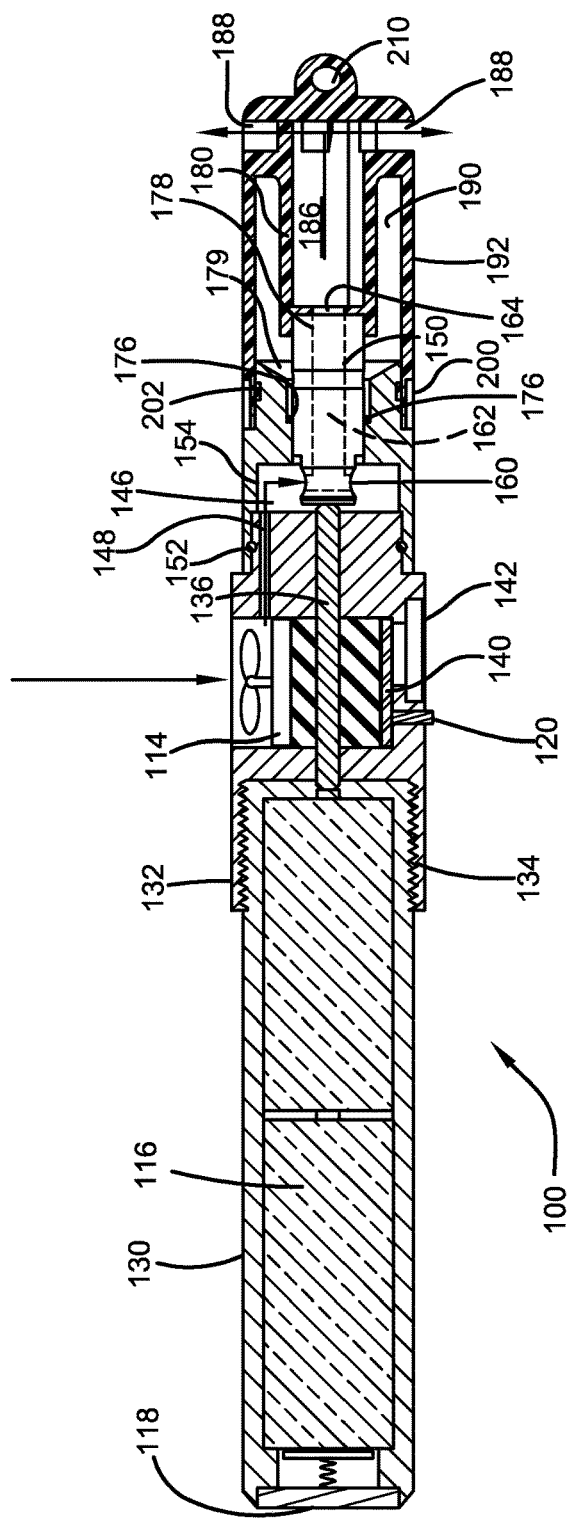

The different configurations of the vaporizing device of the disclosure are indicated generally by the numeral 100 in the accompanying drawings. When assembled for use, each of these configurations generally includes a power source, a heating device, and a reservoir that contains a liquid scent material that vaporizes into an airborne scent that can be used as a lure designed to attract hunting game, as a repellant, as an air freshener, or as a scent eliminator. Device 100 can be provided to the user without a power source with the power source being supplied by the end user. Some of the configurations include an airflow generator such as an electric fan, an air pump, a canister of compressed gas, or a squeezable bladder that is used to create a flow of air or gas that distributes the vaporized scent material from device 100. One configuration is operated by an on-off switch which can be activated manually or with a remote control. Another configuration includes a timer that controls the operation of the device. A further configuration includes a sensor that activates the device when an airflow through the device is detected. An option is to provide a timer that is programmable by the user. The timer controls the creation and distribution of the vaporized scent material. These power options can be used alone or in combination. One configuration provides a refillable liquid cartridge while another configuration provides a sealed liquid cartridge that is removed and replaced after depletion. The cartridge carries the liquid scent material that is vaporized. One configuration of the cartridge simply includes the liquid composition that is vaporized. Another configuration of the cartridge includes the liquid composition as well as the burner element. The cartridges are selectively connectable to the other components or another component of device 100 to allow the user to readily recharge the device for continued use. These general elements of device 100 may be used alone or in combination with each other and the other elements described below to define the different configurations of device 100.

Although the following descriptions refer to the exemplary configurations of FIGS. 1-5, the descriptions are also relevant to the other configurations disclosed herein and, as noted above, similar numbers refer to similar parts of the configurations. Device 100 includes a removable and replaceable cartridge 110 and a base 112. Cartridge 110 carries the liquid scent material that is vaporized to form the airborne vaporized scent material which can be used as an aromatic hunting lure, a cover scent, a repellent scent, a room or automobile air freshener, or a scent eliminator. In this exemplary configuration, cartridge 110 also carries a burner that functions as the heating device that vaporizes the liquid scent material. The heating device can be rapidly heated to a temperature sufficient to rapidly vaporize (less than one to three seconds) the liquid scent material that is in close proximity or in contact with the heating device. The heating device can be heated to a temperature of 390-480 degrees Fahrenheit. In one exemplary embodiment, the liquid scent material is heated to a temperature sufficient to change the liquid scent material from the liquid state to the aerosolized vapor. Other temperature ranges can be used to vaporize the liquid scent material.

Base 112 carries an airflow generator in the form of an electrically-powered fan 114 that creates a flow of air that is delivered to cartridge 110 to distribute the vaporized scent material from device 100. Base 112 also carries a power source 116. Optionally, base 112 includes an on-off switch 118. Additional options carried by base 112 include a controller 120 that can be in the form of a programmable timer that provides the user a selection of preset operating modes or a programmable controller that allows the user to customize the operation of device 100 to match the hunting conditions.

Base 112 carries a power source 116 such as a battery or a plurality of batteries which can be disposable or rechargeable. Power source 116 can be removable. Power source 116 is carried by a power source housing 130 that forms part of base 112 and can carry the optional on-off switch 118. Switch 118 can be located at the lower end of device 100 and is in the form of a push button style on-off switch or a twisting or rotating-style switch.

In one configuration, to turn on the unit, the user presses and holds the button 118 on the control center 120 for five seconds. The user then immediately chooses the disbursement interval, by pressing the button 118 on the control center 120 briefly. A light will come on immediately followed by the unit indicating a five second scent disbursement. This light can be any one of the lights or a combination of all lights. Three options of adjustment are indicated by the color of light on the control center 120. Red: one minute intervals between scent disbursements. Yellow: three minute intervals between scent disbursement. Green: five minute intervals between scent disbursement. To turn the unit off, the user presses and holds the button 118 on the control center 120 for five seconds. All lights will turn off and scent disbursements will stop.

The connection between power source housing 130 and fan housing 132 of base 112 functions as the negative ground for the power circuit of device 100. The connection between housings 130 and 132 can be a threaded connection 134 or a snap-together connection. A seal in the form of an O-ring can be provided to make the connected water-resistant or water-proof.

In order to form this part of the electric circuit of device 100, electrically conductive elements are provided in base 112 that are in electrical contact with the negative side of power source 116. In the exemplary configuration, housings 130 and 132 are fabricated from an electrically conductive metal and the housings themselves define part of the electrical circuit. In other configurations, housings 130 and 132 can be fabricated from a material that is electrically insulating and conductive elements are be carried by each housing 130 and 132 to define the negative side of the electrical circuit.

The positive side of power source 116 is contacted by an electrical connector 136 that either extends into power source housing 130 or is recessed within fan housing 132. These positive and negative sides of the electrical circuit provide the electrical power for fan 114, controller 120 and the vaporizing coil of device 100.

The use of a removable power source 116 carried by housing 130 allows charged replacement power sources 116 to be quickly added to fan housing 132 as needed. The removable power source housing 130 allows optional attachments such as flashlight attachments, power adapters for charging phones, radio attachments, and other powered devices to be used with power source housing 130. In one optional configuration, switch 118 is disposed on the side of housing 130 and a flashlight attachment can be selective added to the end of device 100.

In one configuration, power source 116 is integrated into housing 130 such and is not readily removable from housing 130. Such a power source 130 can be a rechargeable-type of power source 116. The user can swap housings 130 in the field in a situation where the power is low. The housing can include a charging port.

Figure 10:
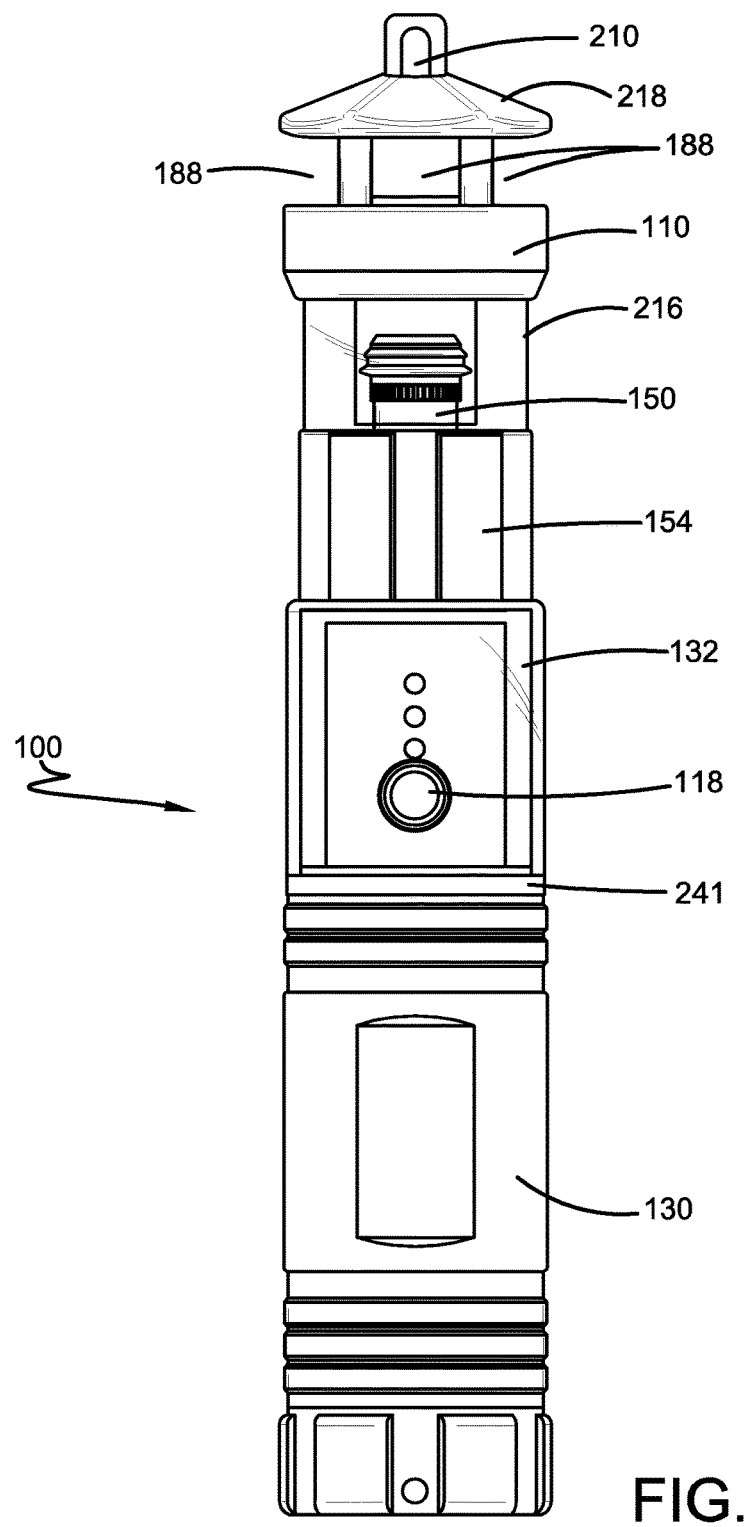
Figure 11:
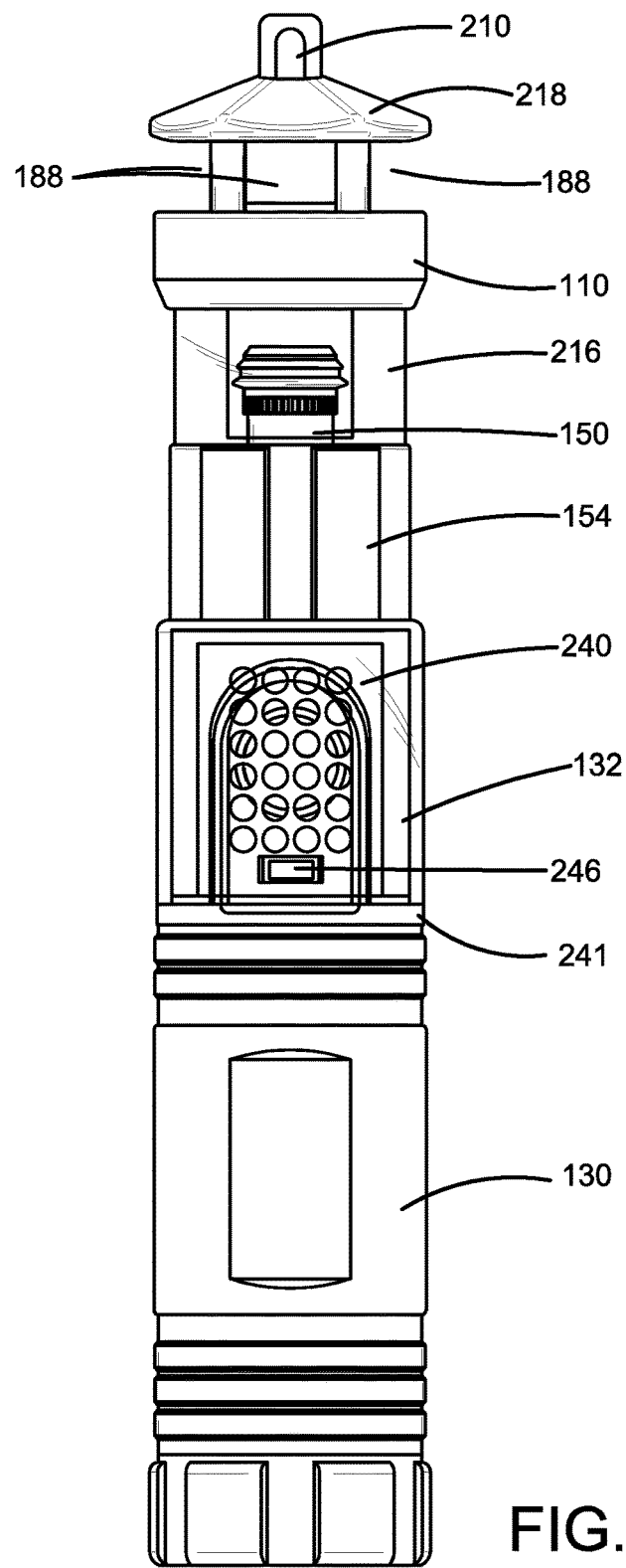
Figure 12:
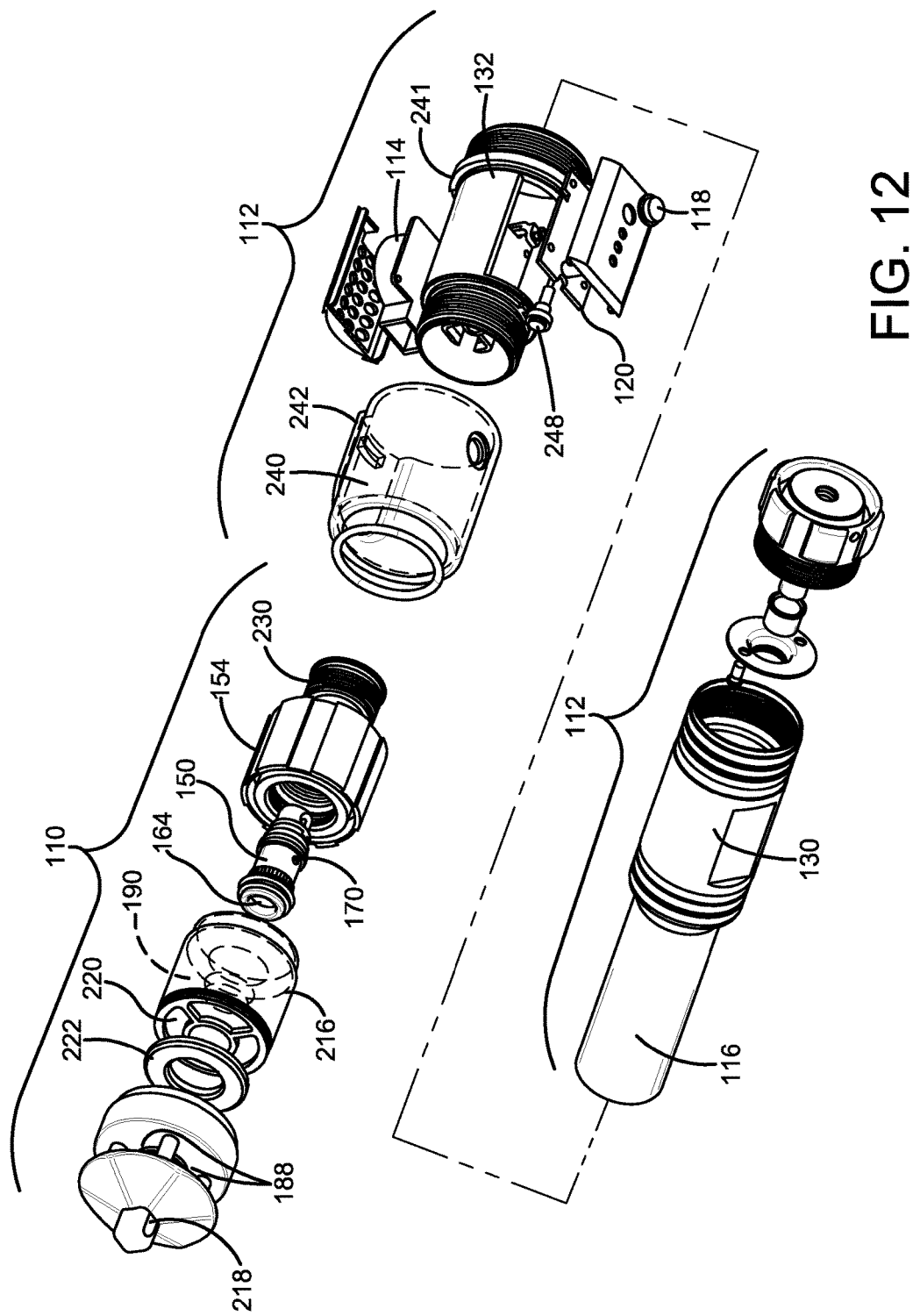
Figure 13:
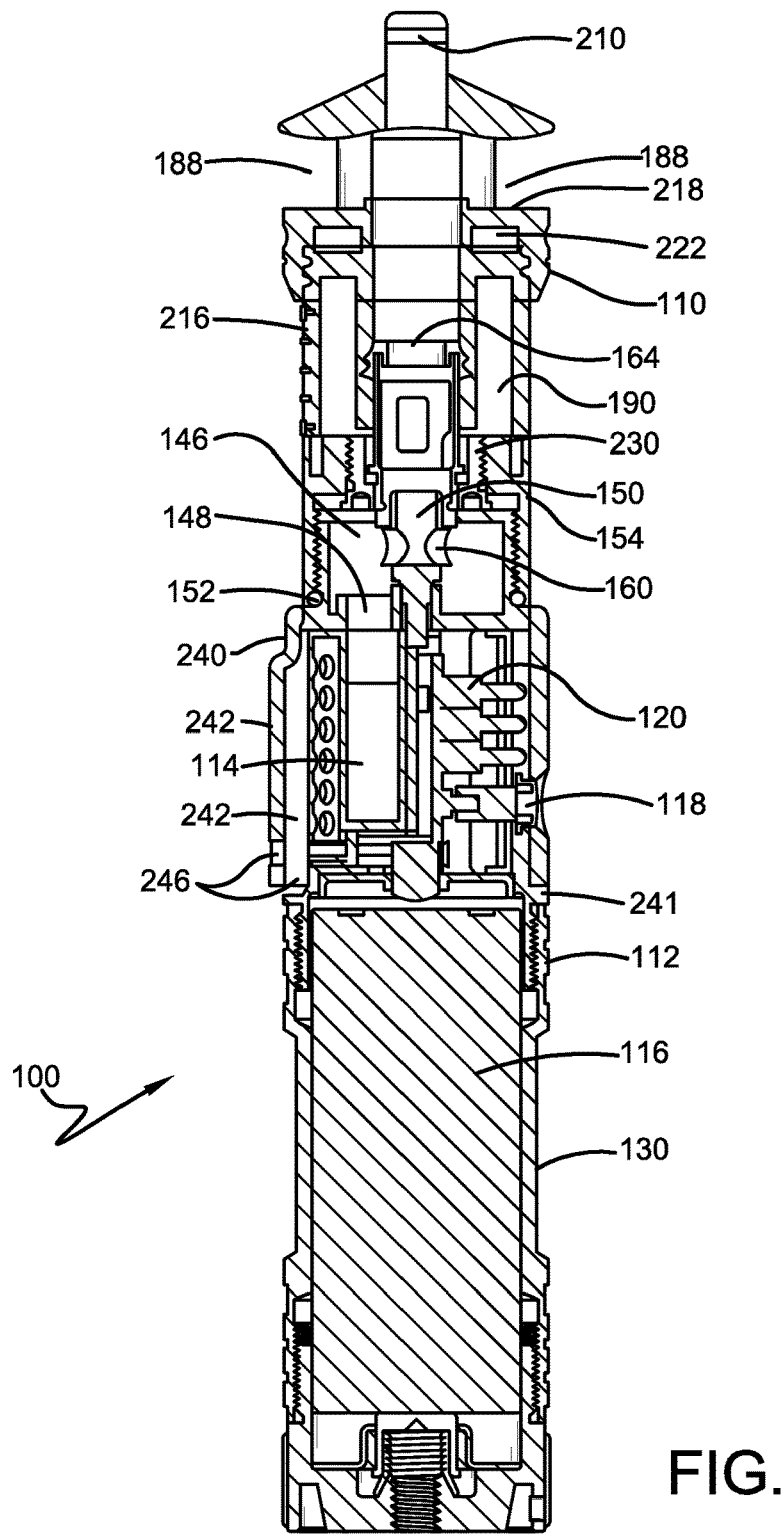

Device 100 can be provided in a simple on-off configuration wherein device 100 forms and dispenses vapor when the users turns device 100 on and stops when the user turns device 100 off. Device 100 can be provided with controller 120 that provides operating configurations that are more useful for some hunting situations. In the configuration depicted in FIG. 2, controller 120 includes a single button (switch 118 is used in the configuration of FIG. 10) and a plurality of indicator lights that indicate the operating condition of device 100. Each operating condition is preprogrammed for a different distribution timing pattern. For example, the first condition can be a long continuous distribution of vapor (such as ninety seconds) followed by ninety minutes of short bursts (such as ten seconds) spaced apart every three minutes. The second configuration can be set to distribute medium bursts (thirty seconds) at longer time intervals (every ten minutes) for an extended time (such as two hours). The third and fourth conditions can have other variations such as short-long-short and very long-very long-very long. Programmable controller 120 allows the user to define the distribution pattern of device 100. Controller 120 allows the user to control the timing of the vapor distribution, the time intervals between distributions, and the volume of the vapor distribution. Controller 120 can include a programmable circuit board 140 that includes a timer. The settings of controller 120 can be changed through push buttons accessible to the user (three button are depicted as examples—more or fewer can be used). A visible screen 142 can be used to display the settings to the user. In other configurations, a wireless communications circuit is used to allow the user to communicate with controller 120 through WIFI, radio frequency (RF), or Bluetooth communications protocols such that device 100 can be set up through software on a user's phone, another mobile computer, or a remote control. An exemplary setting for the operation of the device is to vaporize for three seconds and then turn off for ninety seconds when the sequence is repeated. This sequence can be set to repeat a number of times or for a length of time as desired by the user.

Fan housing 132 defines one or a plurality of air channels 148 for the air flow created by fan 114. Air channels 148 extends from the exit of fan 114 to the upper end of base 112. When cartridge 110 is connected, the outlet of air channel 148 is in communication with a plenum 146 that receives a lower end portion of the burner 150. The removable and replaceable cartridge 110 contains the liquid that is vaporized by device 100 and the burner 150 that, when powered or energized, is adapted to vaporize a selected volume of the liquid. Burner 150 defines an air inlet 160 that is in fluid communication with plenum 146 when cartridge 110 is installed. The air flow from fan 114 pressurized plenum 146 causing air flow into inlet 160 and through an air flow channel 162 defined by burner 150 from inlet 160 to its outlet 164.

Before cartridge 110 is connected to fan housing 132, cartridge 110 is substantially sealed such that the user is not readily exposed to the liquid during the transport and storage of cartridge 110. A removable seal can be provided over the lower end of cartridge 110. This seal is either removed by the user or pierced by base 112 during the installation of cartridge 110. Another configuration only seals air inlets 160 with a removable or meltable seal. The upper end of cartridge 110 can be sealed with its own removable seal or the top portion of cartridge 110 can be rotated between a sealed condition and an open condition.

When cartridge 110 is installed, a gasket, seal, or O-ring 152 forms a seal between the burner holder 154 and the top of fan housing 132. The connection between burner holder 154 and fan housing 132 can be a snap fit, a threaded connection, or a slide and twist locking connection similar to a bayonet connection. In the configuration wherein the installation of cartridge 110 is designed to pierce the lower seal of cartridge 110, the remaining portions of that seal remain on cartridge 110 and form seal 152 when the cartridge 100 is fully seated on fan housing 132.

Burner 150 defines a liquid scent material inlet 170. Within burner 150 in fluid communication with both channel 162 and inlet 170 is a heating element 172 and a wick 174. Heating element 172 is an electric resistive heating-style element (burner coil) that creates heat when electric current is passed through element 172. Wick 174 limits the amount of liquid that is brought into contact or proximity with heating element 172. Wick 174 can be a screen having small openings or an absorbent material. Electricity is delivered to heating element 172 through burner 150 and the circuit is formed through burner holder 154.

Burner 150 is seated in burner holder 154 against an inner shoulder 155 defined by burner holder 154. This connection can be used to form the negative electrical connection between burner holder 154 and heating element 172. Burner 150 can be held in place by being sandwiched between shoulder 155 of holder 154 and end cap 182. A burner cap seal 178 forms a seal between burner 150 and end cap 182. Alternatively or in combination with the sandwiched fit, burner 150 can be held by a friction fit, a threaded connection, or a snap fit. Burner 150 defines a shoulder 176 that seats against inner shoulder 155 of burner holder 150. A seal is disposed between burner 150 and the inner surface of burner holder 154. This connection provides that air inlet 160 is in fluid communication with plenum 146 of burner holder 154. The upper end 179 of burner holder 154 is funnel shaped to direct the liquid into inlet 170.

Burner 150 extends to engage a central portion 180 of end cap 182. Central portion 180 defines a vapor distribution channel 186 of end cap 182. End cap 182 defines a plurality of vapor outlets 188 that allow the vapor to be distributed about the entire perimeter of the device.

End cap 182 defines a liquid holding chamber 190 that holds the liquid aromatic lure material. Inlet 170 of burner 150 is exposed to the liquid in chamber 190. Chamber 190 is defined between the outer surface of central portion and the inner surface of the outer wall 192 of end cap 182. Chamber 190 is thus substantially ring-shaped and surrounds vapor distribution channel 186. End cap 182 is mounted to burner holder 154 with a mounting collar 200 by threads, snap fit, adhesive, or weld/fusion. A seal such as an O-ring 202 can be used as needed.

End cap 182 can define a mounting hole 210 for a lanyard that keeps device 100 in a generally upright configuration so that any liquid in the liquid holding chamber 190 is disposed against the heating element 172 or the wick 174 for the heating element 172 by gravity.

Cartridge 110 is used and discarded. Heating element 172 eventually burns out which allows burner 150 to be disposed with cartridge 110. Disposable cartridges 110 allow the user of device 100 to stay out of contact with the liquid lure and does away with the problem of refilling device 100. When device 100 is empty, the user simply removes cartridge 100 by disconnecting burner holder 154 from fan housing 132. A new cartridge 110 is added and device 100 is ready to use.

In an alternative configuration, the replacement cartridge does not include burner 150. In this configuration, end cap 182 is removed after it is used and a full end cap 182 is replaced onto burner holder 154.

In another alternative configuration, end cap 182 has a refill opening 220 that allows the user to refill liquid into chamber 190 as needed. This configuration is depicted in FIGS. 7-13 and 14-15 wherein end cap 182 is provided in first 216 and second 218 portions. First portion 216 defines liquid holding chamber 190 and defines refill opening 220. Second portion 218 screws onto first portion 216 and seals opening 220 when tightened. A flexible seal 222 (FIG. 12) can be used to seal opening 220. This configuration allows chamber 190 to be refilled with the liquid scent material.

Figure 14:
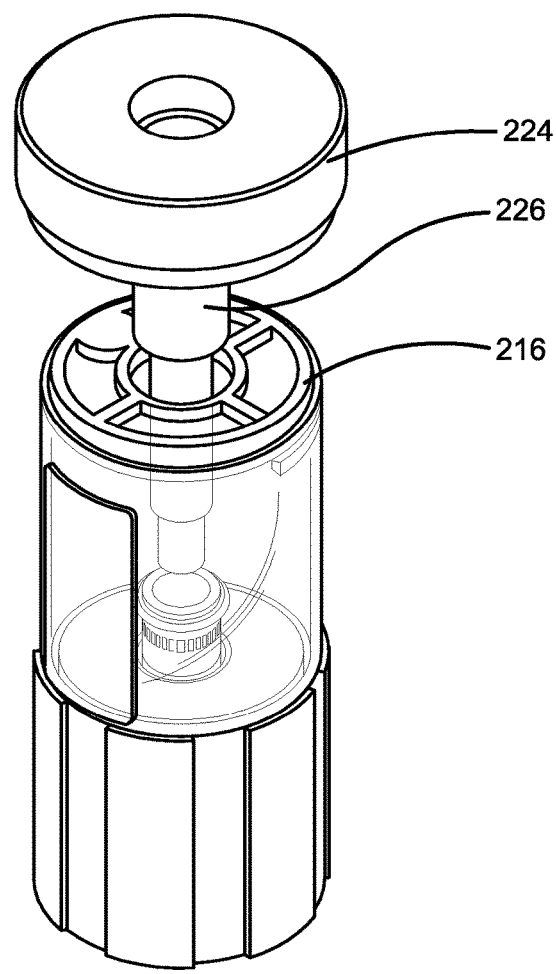
Figure 15:
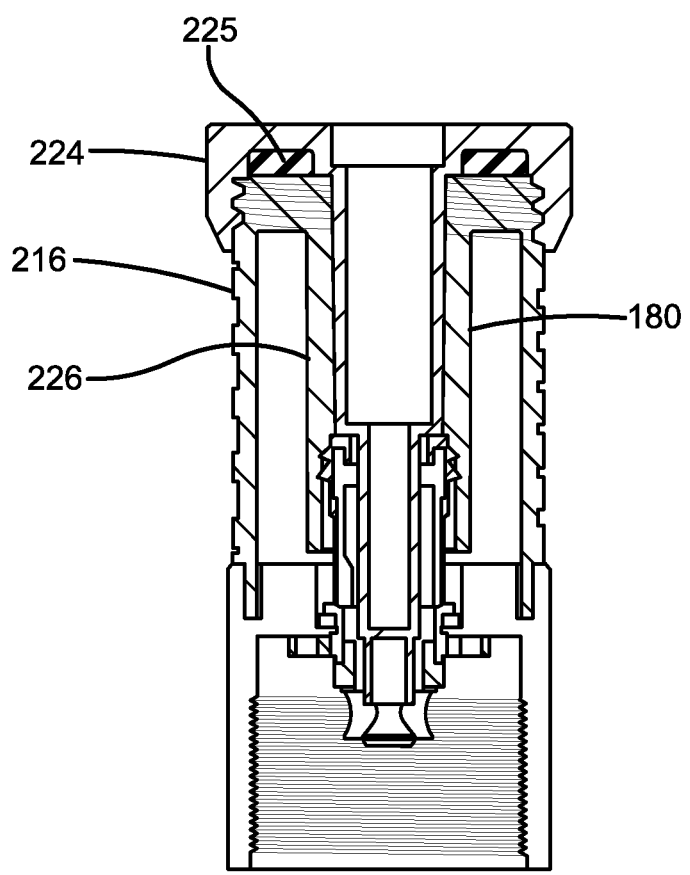

FIGS. 14-15 depict a sealing cap 224 that is connected to first portion 216 of end cap 182 when second portion 218 is removed. Sealing cap 224 has a first disc-shaped portion 225 that sits on top of first portion 216 to seal liquid holding chamber 190. Sealing cap 224 includes threads defined along the inner surface of an outer flange that cooperate with the threads on first portion 216 to secure sealing cap 224 with a threaded connection. Sealing cap has a second elongated portion 226 that extends into first portion 216 to slide into burner 150 (shown in FIG. 15) to close off inlet 170. Second elongated portion 226 can extend to close off inlet 160. Optionally, a second cap can be used over the lower end of burner 150 if desired. When threads are not used, second elongated portion 226 can frictionally engage central portion 180 to connect sealing cap 224 to first portion 216. The lower end of second elongated portion 226 sealingly engages burner 150 to form the seal. Sealing cap 224 can be made from a resilient material such as rubber to allow it to compress when engaged with first portion 216 to form a liquid-tight seal.

In the configuration of FIGS. 10-16, burner 150 is connected to burner holder 154 with a threaded connection between a threaded burner nut 230 and burner holder 154.

FIGS. 16 and 17 depict the cartridge with the manner in which the burner 150 is mounted to the cartridge with a threaded burner mount 154 and nut 230 and the key 232 that can be used to install and remove burner 150. Key 232 can double as a promotional item. As described above, the upper end of burner 150 engages and seals with central portion 180. Threaded burner nut defines at least two spaced key holes that receive corresponding key prongs on key 232 to allow the user to rotate threaded burner nut 230 with key 232. A seal 234 is provided between nut 230 and burner holder 154 which, in cooperation with the threads, seas the lower end of chamber 190. This seal can also be compressed to function as a locking device for the threaded connection.

FIGS. 10-18 depict an alternative version of power source housing 130 and fan housing 132 with an exemplary configuration for a single switch 118 used to control device 100. Different operational modes are selected by the number of times switch 118 is depressed or by the length of time switch 118 is held down.

FIGS. 10-18 depict an optional protective housing 240 disposed around a portion of fan housing 132 and covering the fan intake opening of fan housing 132. In this configuration, protective housing 240 is transparent to allow the user to view indicator lights on controller 120. Switch 118 extends through housing 240 to allow the user to manually change the settings. Switch 118 defines a seal with the opening in housing 240. In configurations wherein controller 120 communicate wirelessly with a mobile computer, switch 118 and the opening in housing 240 can be eliminated. Housing 240 can form a sealed connection with a flange 241 projecting from housing 132. Housing 240 has a raised section 242 that defines an inlet plenum 244 over the fan inlet. The raised section defines the air inlet for the fan. A perforated grid can be disposed over the fan inlet. A fan inlet opening 246 can be defined by housing 240 or though flange 241 or both. Housing 240 protects controller 120 and fan 114 from liquids and other debris.

Controller 120 can control the delivery of power to burner 150 or an airflow sensor 248 can be used to active burner 150 whenever fan 114 is generating an airflow. When sensor 248 is used, controller 120 controls the operation of fan 114 and the delivery of power to burner 150 is controlled by sensor 248. Sensor 248 can operate by being moved by the airflow to provide an electrical connection.

Figure 18:
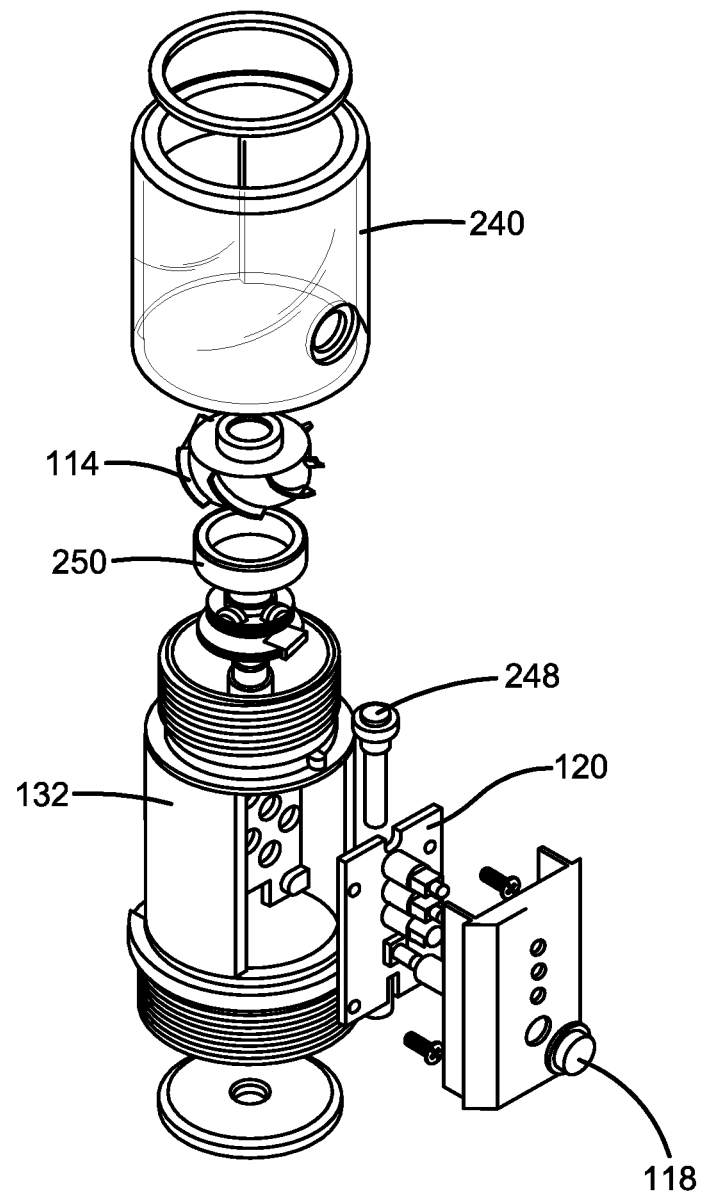

FIG. 18 depicts an alternative configuration for the fan housing 132 wherein fan 114 is mounted with its axis of rotation parallel to the longitudinal axis of device 100. A magnetic mount 250 is used to hold fan 114 in place. Magnetic mount 250 is provided as a magnetic ring over which fan 114 is seated. The air is pulled into fan housing 132 through a plurality of openings disposed across from controller 120. In this configuration, the lower end of housing 132 carries sealed a water proof pad to prevent water from entering the air openings and moving into the battery housing.

FIGS. 19-28 disclose configurations wherein a manually-operable airflow generation device 260 is used to create vapor distribution airflow through device 100 to distribute the vapor created by burner 150. Manually-operable airflow generation device has first and second configurations. Device 260 can be a squeezable flexible bladder that, when squeezed from the first to the second configuration, reduces its interior volume to expel a portion of the air within the bladder out of an outlet. The manual airflow generation device also can be a manually-operated fan such as a plurality of fan blades that spin when a crank is turned or when a trigger is pulled. Another configuration includes a bellows-style airflow generator that creates an airflow when elements pivot toward each other.

In each of the configurations of FIGS. 19-28, burner 150 of device 100 can be activated with a manually-operated power button or a sensor that senses airflow, pressure changes, temperature change of the airflow or senses a change in the dimensions of the bladder wall of manually-operable airflow generation device 260. The sensor can be a biased member such as a plunger or membrane that moves in reaction to the airflow and forms an electrical connection between the power source and the burner to rapidly vaporize the liquid scent material in response to the airflow. In one embodiment, the airflow created by the bladder moves a biased member that brings an electrical contact into electrical contact with another electrical contact to complete a circuit and power burner 150. In these configurations, burner 150 can be provided in the configurations described above or as an electrical resistive heating element such as a coil of thin wires or strands of metal.

In each of the configurations of FIGS. 19-28, a resilient bladder 260 is used to generate the airflow through device 100. Each bladder 260 is made from a resilient material that can be deformed when a compressive force is applied to the outside of the bladder wall. The bladder wall can be designed to automatically return to its uncompressed state when the compressive force is released. Alternatively, a resilient foam material 262 can be disposed inside bladder 260 to help bladder 260 to maintain its shape and to help bladder 260 return to its resting condition after being squeezed. In other configurations, a mechanical spring is used to help push the bladder wall back to its resting condition. These items can be used alone or in combination with one another or in combination with the wall material of the bladder itself. Also, each bladder wall can be configured to return to the resting position through the resiliency of the material used to form the bladder wall combined with the shape or configuration of the bladder wall itself.

Also in the configurations of FIGS. 19-28, each bladder 260 can be provided with a one-way valve 274 and/or a manually-operated valve 276. A one-way valve 274 allows air to flow into bladder 260 but prevents air from exiting bladder through valve 274. Although valve 274 can be disposed anywhere on bladder 260, valve 274 can be carried by bladder 260 at a portion of bladder 260 that is not substantially deformed when bladder 260 is squeezed. Such a portion can be the bottom wall of bladder 260. As an addition or as an alternative to valve 274, an opening 276 can be defined by the wall of bladder 260. Opening 276 functions as a manual valve that must be covered by the user's finger when squeezing to force air toward burner 150. A benefit of opening 276 is that it prevents unintentional actuation of device 100 by allowing air flow out of bladder 260 when the user unintentionally squeezes bladder 260. This allows device 100 to be carried in the user's pocket without worry about undesired activation.

In any of these configurations, an additional one-way valve positioned downstream of the outlet of bladder 260 can be used as an option to prevent back flow from burner 150. An example of this configuration is depicted in FIG. 20.

Each of the configurations of FIGS. 19-28 uses a version of an electric vaporizer 280. Electric vaporizer 280 can include a power source 270 or can be removably connected to power source 270. Electric vaporizer 280 includes burner 150 in the configuration described above or as a stripped down configuration with just the wick material and burner coil. Electric vaporizer 280 also includes an air inlet 282, a supply of liquid scent material 284, and a vapor outlet 286. Electric vaporizer 280 can be disposable or refillable. Electric vaporizer 280 can be energized by a manual switch 288 or a sensor 290 as described above.

Figure 19:
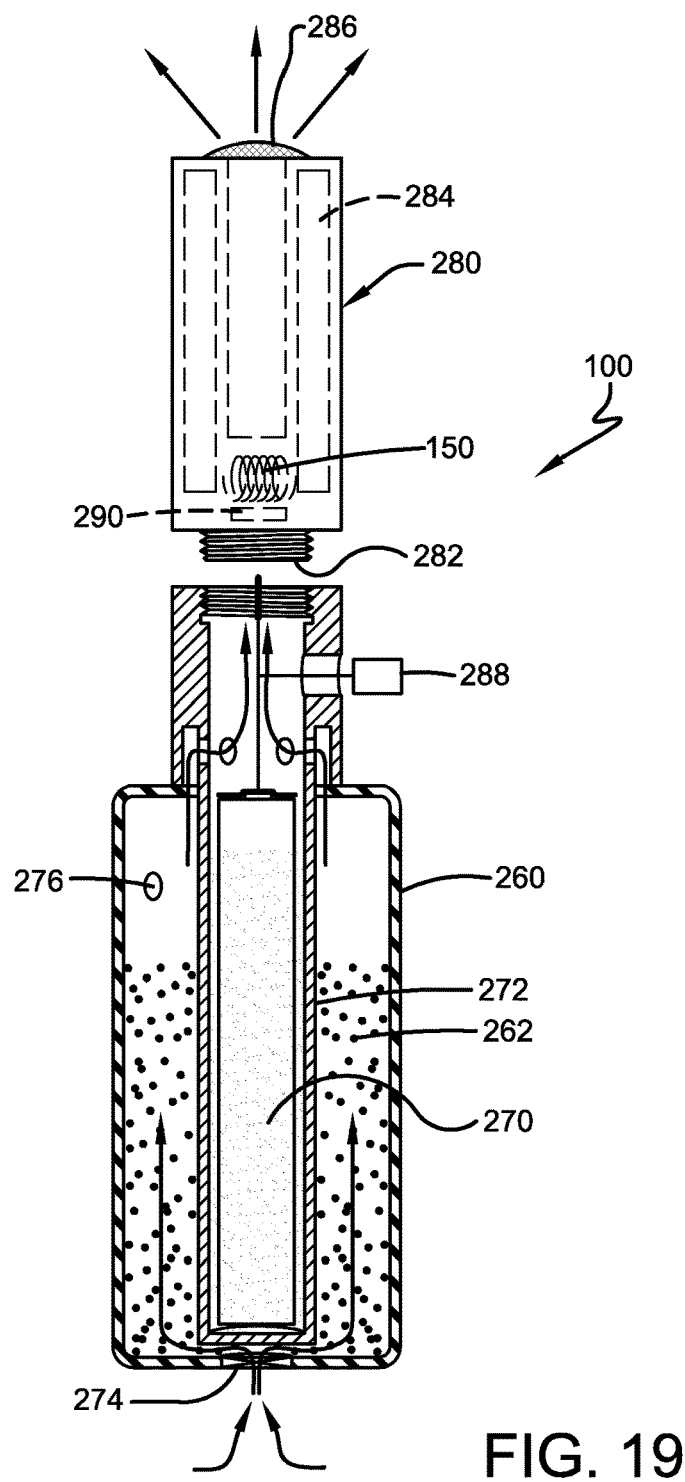

In the configuration of FIG. 19, a power supply 270 is disposed in a power supply housing 272 which is substantially surrounded with a squeezable air bladder 260 that, when squeezed, delivers an airflow to burner 150. Power supply housing 172 selectively receives electric vaporizer 280 which is connected through the threaded connection depicted in FIG. 19, a snap fit connection, or a friction connection. In the FIG. 19 configuration, a power lead is provided to supply power to vaporizer 280. In the FIG. 19 configuration, bladder 260 substantially surrounds power supply housing 272 with at least a majority of electric vaporizer 280 being disposed outside bladder 260 in an extended configuration where it can be readily replaced.

Figure 20:
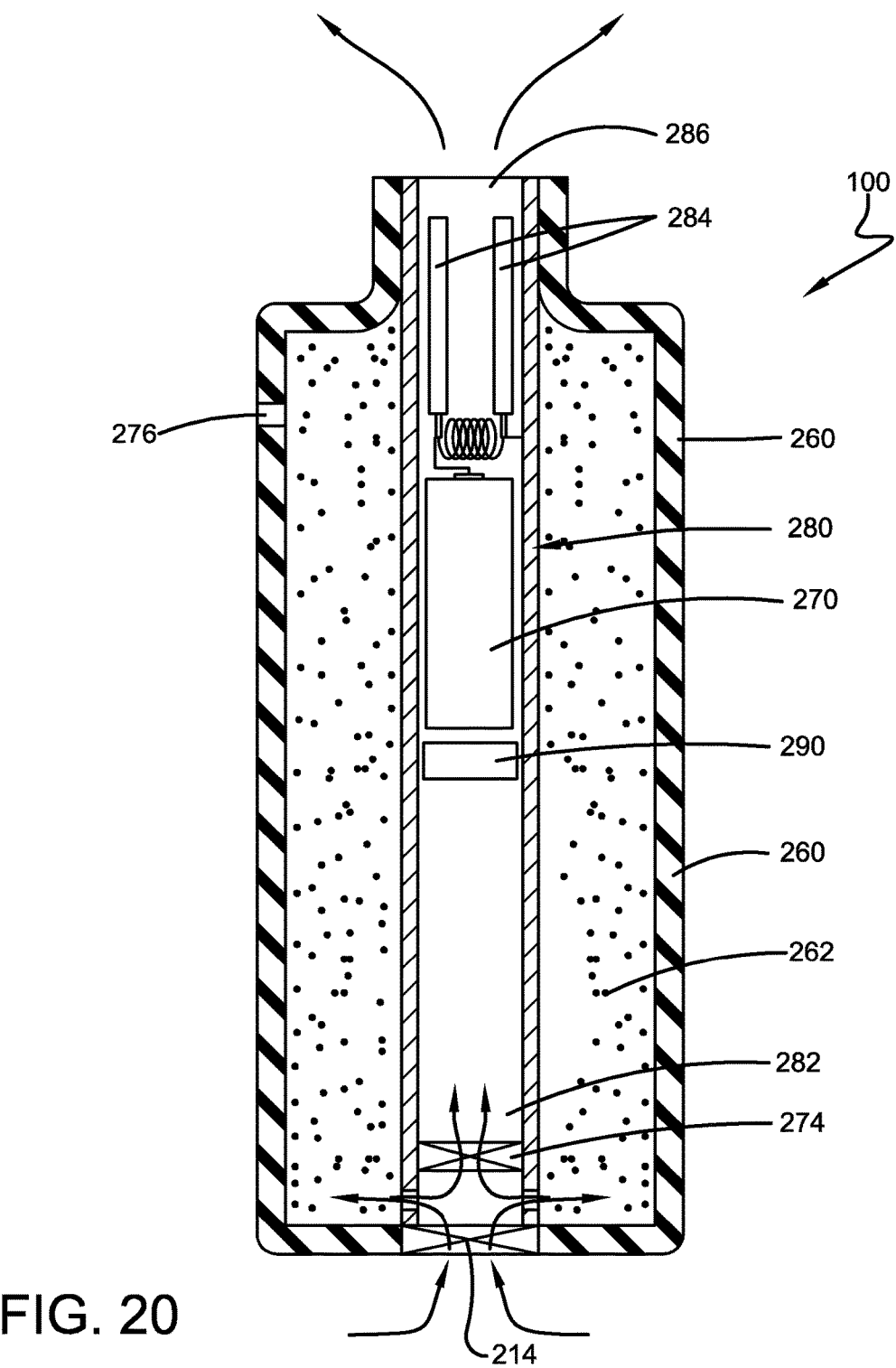
FIG. 20 is a view of another exemplary configuration with a hand-powered squeeze-type airflow generator.

In the configuration of FIG. 20, the bladder 260 surrounds the entire length of electric vaporizer 280 and power supply 270. The main air intake valve 274 is disposed at the bottom of device 100. A sensor 290 such as an air pressure sensor is used to active the burner coil when the user squeezes the bladder 260 to generate airflow into the coil. The FIG. 20 configuration includes a second valve 274 to prevent backflow.

Figure 21:
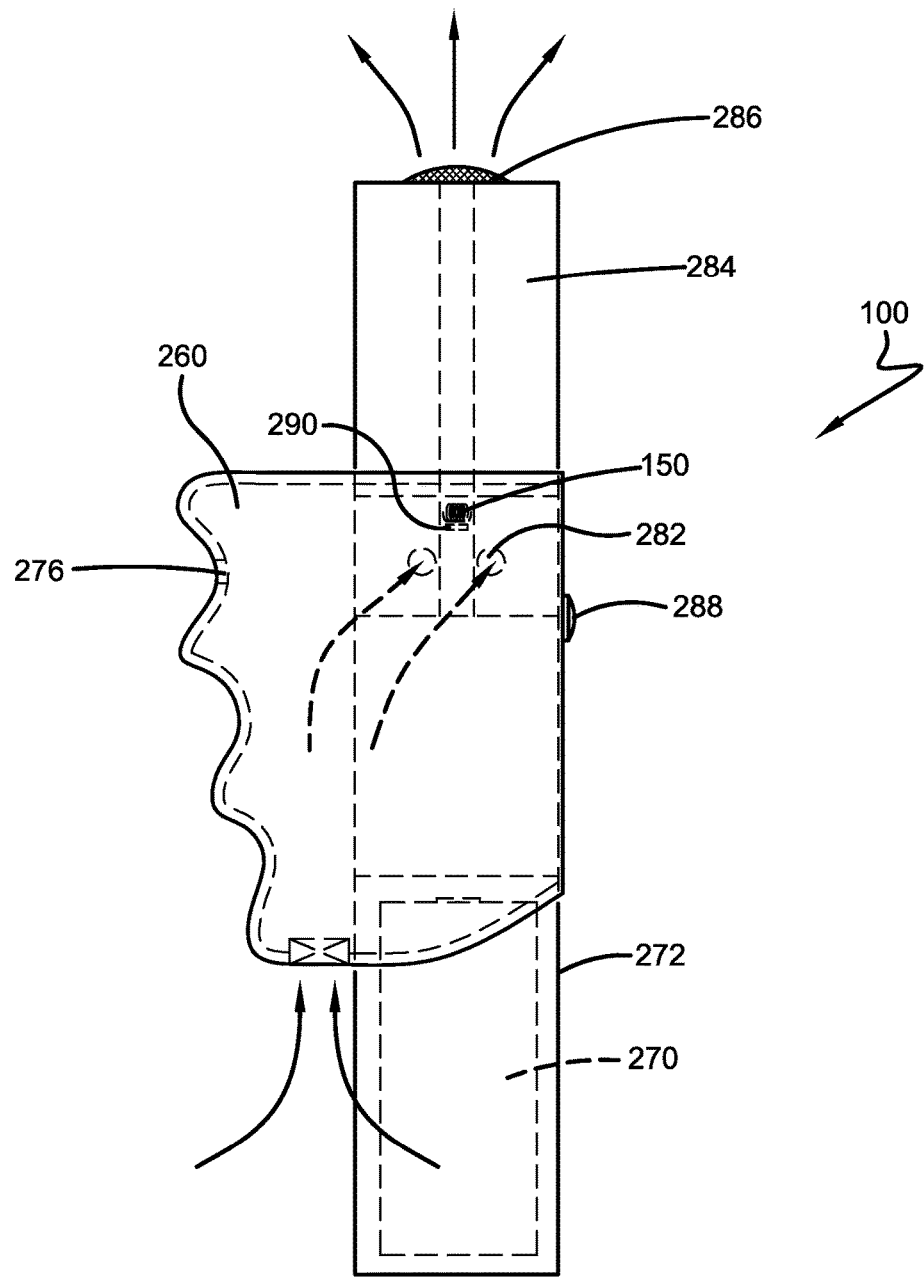
FIG. 21 is a view of another exemplary configuration with a hand-powered squeeze-type airflow generator.

In the configuration of FIG. 21, the airflow generator bladder 260 is disposed at the location of the fan inlet of FIG. 1. In this configuration, the bladder 260 is shaped to fit the user's hand so that the user grips the bladder 260 and the housings with a single hand. When a power button 288 is used, the user's thumb or finger can control the power button 288 while the palm of the hand compresses the bladder 260 to generate the airflow to the burner coil 150. A sensor (such as sensor 290) can be used as an alternative to or in addition to switch 288. A valve can be used to control the airflow into bladder 260. A secondary valve can be used to prevent suction back into the bladder from the coil.

Figure 22:
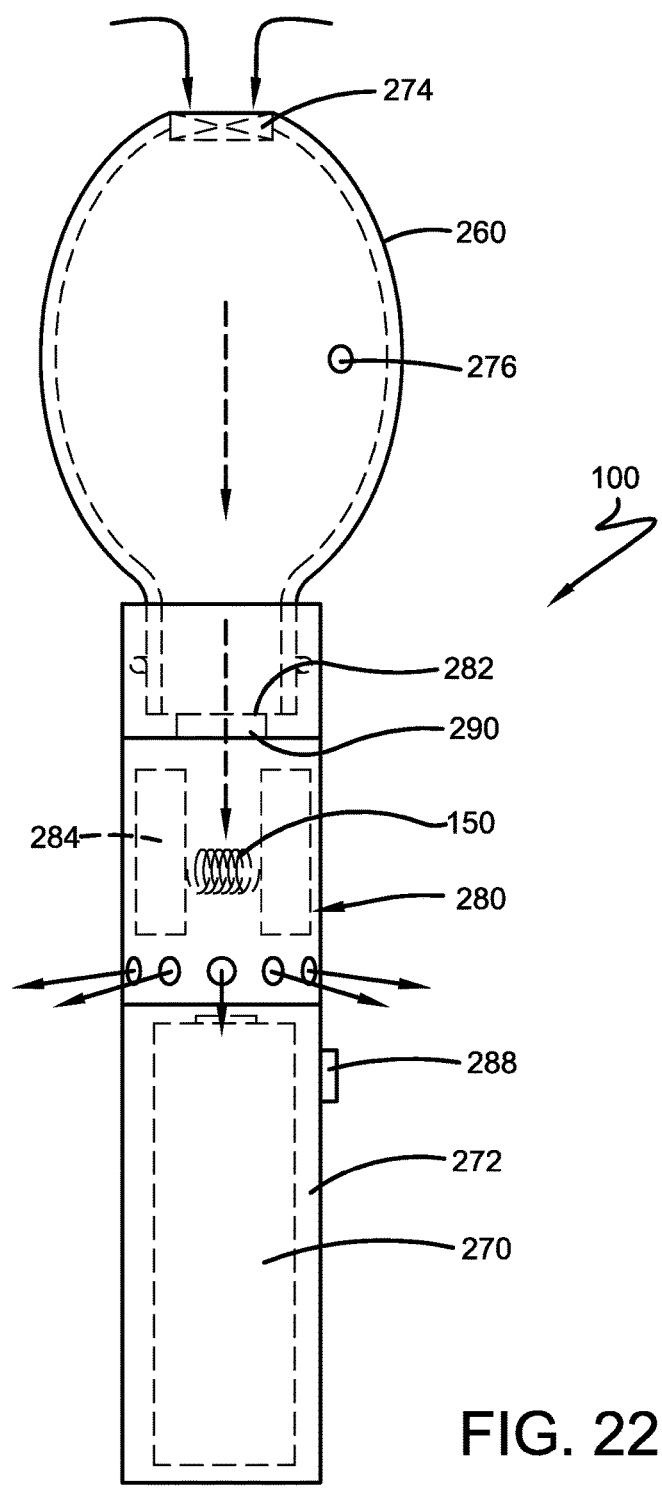
FIG. 22 is a view of another exemplary configuration with a hand-powered squeeze-type airflow generator.

In the configuration of FIG. 22, the airflow generator bladder 260 is disposed opposite the power source 270 and pushes air down through the liquid holding tank 184 and then through the vaporizing coil 150. An inlet valve 274 can be used to refill the bladder 160. In this configuration, power button 288 turns unit 100 to an cony configuration while sensor 290 is used to energize burner 150.

Figure 23:
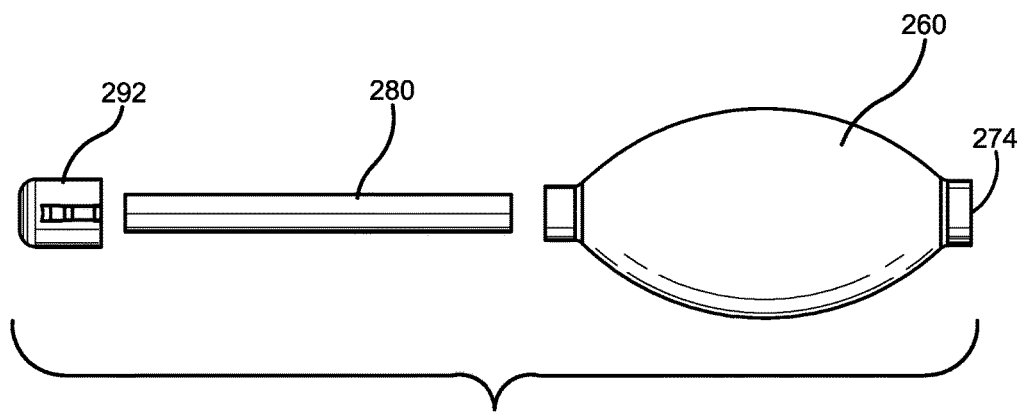
FIG. 23 is an exploded view of another exemplary configuration wherein a hand-powered squeeze-type airflow generator provides the airflow to the device.
Figure 24:
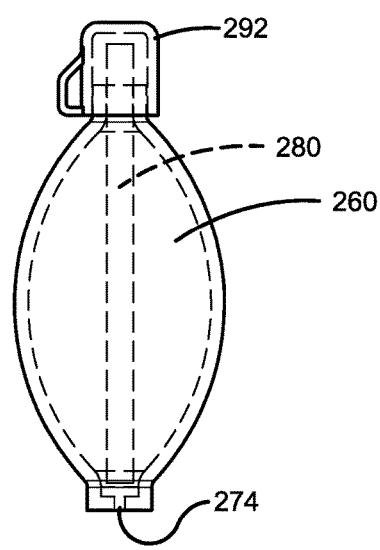
FIG. 24 depicts one exemplary hand-powered squeeze-type airflow generator with a valve to control airflow.
Figure 25:
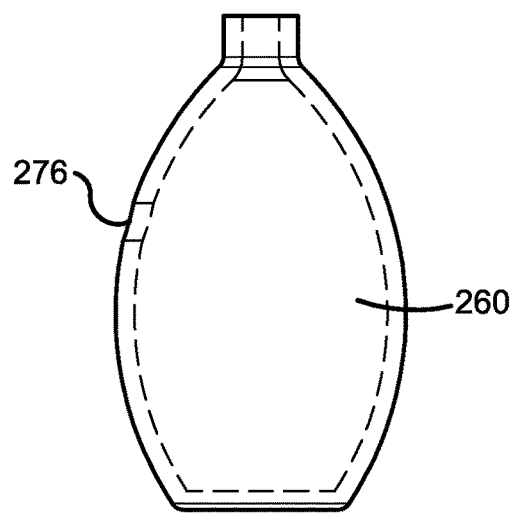
FIG. 25 depicts another exemplary hand-powered squeeze-type airflow generator with a manual valve to control airflow.

FIG. 23 is an exploded view of another exemplary configuration wherein a hand-powered squeeze-type airflow generator is provided in the form of a resilient bladder 260 that provides the airflow to the device 100. In this configuration, bladder 260 is provided with a one-way valve 274 and/or a manual valve 276 that control the airflow delivery to an electric vaporizer 280. Valve 274 allows bladder 260 to refill with air after being squeezed. Valve 276 must be covered with the user's finger or thumb to prevent air from being squeezed out of valve 276. The user then uncovers valve 276 to allow bladder 260 to refill with air. FIG. 24 depicts one exemplary hand-powered squeeze-type airflow generator 260 with valve 274 to control airflow. FIG. 25 depicts another exemplary hand-powered squeeze-type airflow generator 260 with manual valve 276 to control airflow.

Figure 26:
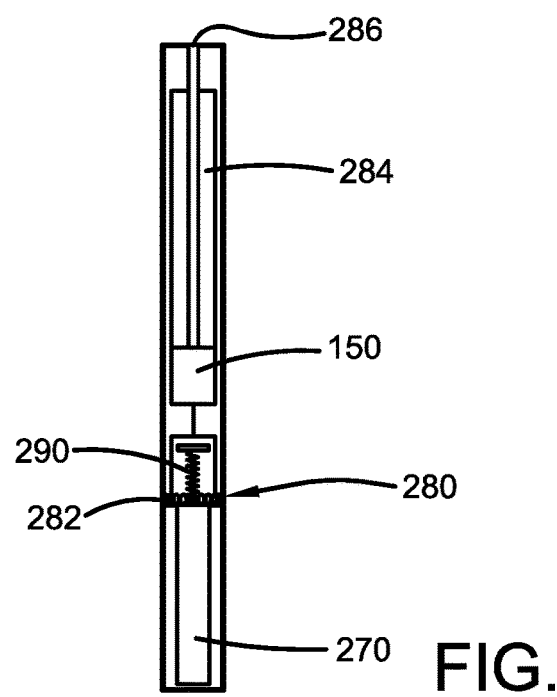
FIG. 26 depicts the electric vaporizer that is used to create the vaporized scent.

FIG. 26 depicts an electric vaporizer 280 that is used to create the vaporized scent material. Electric vaporizer 280 includes a power source 270 such as a battery or rechargeable battery, an airflow passage extending from an inlet 282 to an outlet 286 to allow the airflow generated from bladder 260 to be delivered to a burner 150. Electric vaporizer 280 can include a power button (optional) that energizes burner 150 and/or electric vaporizer 280 includes a sensor 290 (optional) that automatically energizes burner 150 when sensor 290 is subjected to airflow from bladder 260. Sensor 290 can be a biased plunger that moves in response to the airflow to form the electrical connection between power source 270 and burner 150. Sensor 290 also can be an air pressure sensor configured to energize burner 150 in response to an increase in the air pressure in vaporizer 280. The liquid scent material is carried by a liquid holding tank 284 in fluid communication with burner 150. Electric vaporizer 280 defines an outlet 286 to allow the airflow to distribute the vaporized material.

Figure 27:
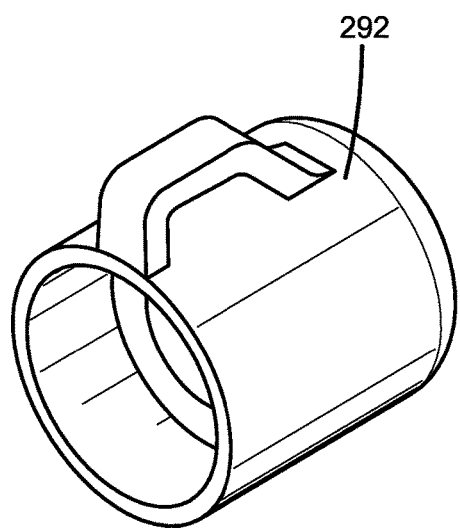
FIG. 27 depicts a cap that can be used on the hand-powered squeeze-type airflow generator or on the end of the electric vaporizer.
Figure 28:
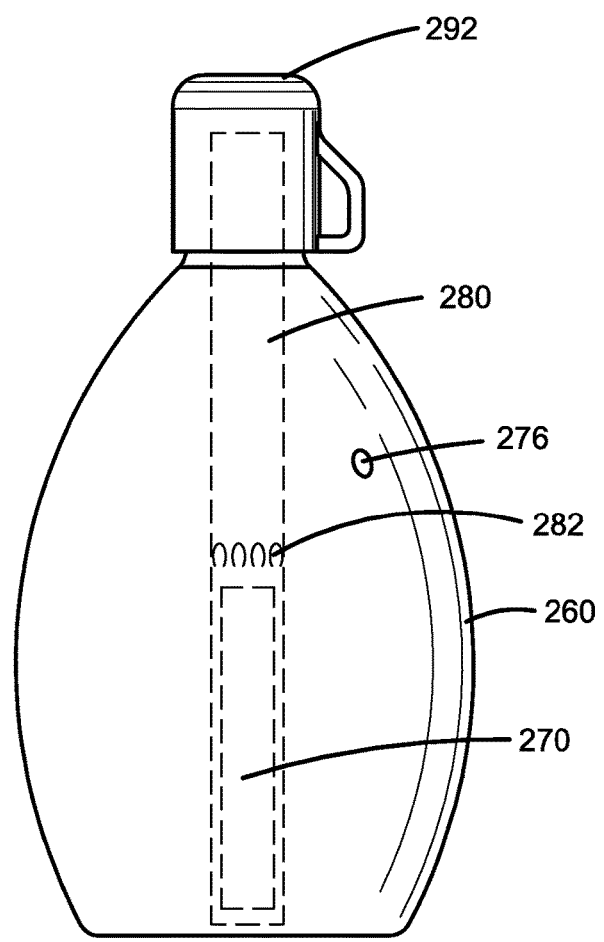
FIG. 28 depicts the cap on the hand-powered squeeze-type airflow generator.

FIG. 27 depicts a cap 292 that can be used to close outlet 286 and/or to provide a lanyard opening to allow the device having cap 292 to be hung from one's belt or coat. FIG. 28 depicts the cap 292 on the hand-powered squeeze-type airflow generator. In this configuration, a majority of electric vaporizer 280 is disposed within a rounded, oval bladder with cap 292 adapted to selectively cover the outlet end of electric vaporizer 280 that extends from bladder 260. Cap 292 can be snap fit, friction fit, or threaded onto vaporizer 280 to secure it in place and to allow the device to be hung from a clip or lanyard. In another configuration similar to the one depicted in FIG. 20, electric vaporizer 280 is disposed entirely inside bladder 260. In this configuration, cap 292 can engage the upper end of bladder to cover outlet 286. In both of these configurations, electric vaporizer 280 is removable and replaceable so that a different electric vaporizer 280 can be installed. Bladder 260 can resiliently engage the outer surface of vaporizer 280 to define a seal. A clamping ring can be provided to tighten the seal.

Electric vaporizer 280 can be used with battery-powered air pump that has a timer controller 120. This unit can be placed in a location and left alone to operate automatically. These can be used to create a scent fence to control wildlife movement or to draw game into a hunt area. The battery-powered air pump can be disposed in a stable base that limits the risk that the device would be tipped over. Vaporizer 280 can be readily detached from the pump with a quick connection that can be a threaded connection, a snap fit, a resilient fit or a friction fit.

An exemplary configuration of such a device is depicted in FIG. 29 wherein the lower inlet portion of electric vaporizer 280 is fit into an adapter 302 to receive an airflow delivered by a base 304. In this configuration, base 304 having adapter 302 allows the mounting of either just electric vaporizer 280 or the entire device 100 depicted in FIG. 30. Adapter 302 is in the form of a tube that extends upwardly from base 304 to receive the lower end of electric vaporizer 280 such that airflow delivered to adapter 302 is delivered to the inlet of electric vaporizer 280. A seal such as a polymeric O-ring can be used to provide a tight connection between electric vaporizer 280 and adapter 302. In other configurations, adapter 302 can be made from a polymeric material that stretches to receive electric vaporizer 280 and forms a seal that is tight enough to direct substantially all airflow delivered to adapter 302 into electric vaporizer 280. In one configuration, the top wall of base 304 defines a recessed area 306 that receives the lower portion of bladder 260 (up to a quarter of the height of bladder 260 can be disposed in recess 306) to seat device 100 of FIG. 24 wherein adapter 302 extends through valve 274 to supply the interior of bladder 260 with airflow. The recessed area 306 can complement that shape of the lower portion of bladder 260 such that base 304 cups and holds and helps support device bladder 260. However, recessed area 306 is not required for the configuration to function. Adapter 302 can be provided with or without recessed area 306.

Base 304 carries an airflow generator 310 in the form of an electrically-powered fan, a valved cartridge of compressed gas, a mechanical bellows, or an air pump (such as a diaphragm pump) that creates a flow of air that is delivered to adapter 302 such that the airflow is delivered to device 100 or directly into electric vaporizer 280 to activate the creation of vapor as described above.

Base 304 also carries a power source 312 such as a battery or a plurality of batteries which can be disposable or rechargeable. Power source 312 can be removable. Optionally, base 304 includes an on-off switch 314. Additional options carried by base 304 include a controller 316 that can be in the form of a programmable timer that provides the user a selection of preset operating modes or a programmable controller that allows the user to customize the operation of the unit to match the hunting conditions. Controller 316 also can be activated remotely with a wireless device such as a handheld computer using cell phone, Blutooth, WIFI, or other communications protocols. Controller 316 also can be activated, deactivated, and switched between operating modes with a radio frequency remote controller that is carried by the user. These options allow this configuration to be used at a location remote from the immediate location of the hunter. The remote control can operate like a garage door opener with one button for power on and one button for power off (or standby). When powered on, the device can dispense vapor continuously until turned off or can operate on a timed schedule.

As above, airflow generator 310 can be used on-demand by the user by turning it on and off with the switch 314 or a remote control unit. Controller 316 also can be provided with distribution timing patterns such as those described above or a pattern that creates and distributes vapor for three seconds followed by sixty seconds of standby with the pattern repeating until the user changes the condition with the remote control or by using switch 314.

Base 304 can include a threaded tripod mount 320 to allow the user to mount this configuration above the ground. Base 304 also includes feet 322 that support base 304 directly on the ground.

A feature of this configuration is noise deadening insulation 324 disposed around airflow generator 310 to ensure the quiet release of the vapor. Insulation 324 can be a foamed polymer insulation material disposed around at least the upper portion of airflow generator 310 but it may be disposed around five sides or substantially surround airflow generator 310. In one configuration, airflow generator 310 is disposed in a chamber defined by walls within base 304 with an airflow tube extending up to adapter 302 through insulation disposed on the outside of the walls.

In each of the embodiments describe above, the liquid scent material that is being vaporized can be a combination of a glycol substance with an aromatic material or a scent-elimination material. The aromatic material can be a solid or liquid animal lure substance. The glycol substance can be a propylene glycol, a vegetable glycerin, a combination of both, and/or a combination of these with water. The animal lure aromatic material can be a liquid or solid animal urine or glandular secretion. The solid materials can be made by dehydration. In any of these combinations, water can be added as needed. The dehydrated urine can be formed by freeze drying, flash drying liquid urine, or otherwise dehydrating the liquid urine to form the additive to the glycol. The aromatic material can be designed to repel animals or insects and can thus be a predator smell or a citronella. The aromatic material can be a cover scent used by a hunter to cover his scent when entering or leaving a hunt area. The aromatic material can be a pleasant-smelling material that one can use to freshen room air or an automobile. These aromatic materials can be clean-smelling materials, flower-based materials, fruit-based materials, pleasant-smelling food materials, pleasant-smelling outdoor smells, spices, tropical smells, and others enjoyable to human users. These can be provided as oils or powders and mixed with the glycol.

In one configuration, the user of the scent material mixes the liquid scent material immediately prior to adding it to a vaporizing device in order to provide a fresh liquid scent material. In this configuration, the components of the liquid scent material are provided in separate containers such as one with the scent components (dehydrated urine or glandular secretion materials or other dry scent materials as described above or a scent oil) and the other being the vaporizable liquid (PG, VG, combination or PG and VG, or combination of these with water). The user mixes the two and agitates until the scent material is dissolved into a vaporizable liquid scent that is fresh when added to the vaporizing device. These can be provided in separate bottles or separate chambers of a container that can be mixed on demand by removing a barrier by displacement or breaking the barrier. In another configuration, the vaporizable liquid can be disposed in the tank 190 or in the electric vaporizer 280 and the user adds the solid scent material or oil before using.

Device 100 has the advantage of only vaporizing the liquid scent material on demand. The device does not waste the liquid scent material by continuously vaporizing unless the user selects continuous operation as an option. The device will function in cold weather and the vaporized glycol-based vapor substance hangs in the air and does not distribute itself in the air as fast as other scent materials. The electric heating element does not create any additional fuel scent through a combustion process. The removable and replaceable cartridges keep the scent fresh and allow the user to readily refill the device without skin contact with the scent liquid. There is also no risk of spilling the liquid. The user can program the device to automatically freshen the scent at intervals.

One method of using device 100 is to provide device with a repellant scent that drives game away from the scent. Device 100 is then used along a boundary or in an area such as a user's yard wherein the user does not want the game to cross or to congregate. The repellant material can include the scent of a predator, a soap, a human, a dog, or the like. The user can set a scent fence line of vaporizing devices timed to form and distribute the vaporized scent at periodic times. This creates a scent barrier than helps keep game from passing through the area. This configuration of the device can be used to deter game such as deer from entering a garden area or a landscaped area where the deer feed on the plantings.

Another use for device 100 is to provide a vaporizable material in device 100 that reduces or eliminates scent particles from the air that is exposed to the vaporized material. This device is used for scent elimination. The disclosure provides a vaporizable mixture that includes a percentage of carbon, charcoal, activated carbon, or coconut shell activated carbon, or palm kernel shell charcoal or a combination of these substances. The combination of these substances with a vaporizable material such as the glycol materials discussed above allow a scent elimination substance to be generated to be used by a hunter to eliminate or reduce scents that can alert game to the hunter's presence.

An optional alternative use for the device is to attach a scent cartridge to the device that creates a pleasant smelling vapor for use in deodorizing a vehicle, a house, clothing, and the like. An advantage here is that by using the removable cartridge, there is no deer urine scent left on the device when a pleasant smelling scent is installed. This is especially true when the cartridges carry their own burner coils. As such, the same device used to distribute the deer urine smell can also be used to distribute a pleasant smelling vapor—such as a vanilla—for the hunter's vehicle on the drive home.

In the foregoing description, certain terms have been used for brevity, clearness, and understanding. No unnecessary limitations are to be implied therefrom beyond the requirement of the prior art because such terms are used for descriptive purposes and are intended to be broadly construed. Moreover, the descriptions and illustrations of the exemplary configurations are examples and the claimed invention is not limited to the exact details shown or described. Throughout the description and claims of this specification the words "comprise" and "include" as well as variations of those words, such as "comprises," "includes," "comprising," and "including" are not intended to exclude additives, components, integers, or steps.

The invention claimed is:

1. An electric vaporizing device for creating and distributing a vapor at a location remote from a hunter to aid the hunt; the device comprising:
   an electric vaporizer having an airflow inlet, a burner, a supply of vaporizable liquid scent material, an airflow channel, and an outlet;
   the vaporizable liquid scent material including at least one of an animal lure aromatic material and a hunting cover scent and at least one of a propylene glycol and a vegetable glycerin;
   the electric vaporizer having a first power source selectively connectable with the burner to energize the burner;
   a base having a second power source, an airflow generator selectively powered by the second power source, and an adapter;
   the airflow generator adapted to selectively deliver an airflow to the adapter; and
   the electric vaporizer being selectively mountable to the adapter with the inlet of the electric vaporizer receiving the airflow provided to the adapter from the airflow generator.

2. The device of claim 1, wherein the animal lure aromatic material includes at least one of an animal urine material and a glandular secretion material.

3. The device of claim 1, wherein the airflow generator can be turned on and turned off with a remote control.

4. The device of claim 1, wherein the adapter is a tube and a portion of the electric vaporizer disposed in the tube.

5. The device of claim 1, wherein the base defines a recess; the adapter disposed at the recess.

6. The device of claim 5, further comprising a collapsible bladder that carries the electric vaporizer; the collapsible bladder being seated in the recess.

7. The device of claim 6, wherein the bladder carries a valve; the adapter disposed through the valve.

8. The device of claim 1, wherein the electric vaporizer includes a sensor that energizes the burner when airflow is delivered to the electric vaporizer.

9. The device of claim 1, further comprising a timer that selectively powers the airflow generator.

10. The device of claim 1, further comprising a noise deadening insulation disposed adjacent the airflow generator.

11. An electric vaporizing device for creating and distributing a vapor at a location remote from a hunter to aid the hunt; the device comprising:
an electric vaporizer having an airflow inlet, a burner, a supply of liquid vaporizable material, an airflow channel, and an outlet;
the electric vaporizer having a first power source selectively connectable with the burner to energize the burner;
a base having a second power source and an airflow generator selectively powered by the second power source;
the electric vaporizer being removably mountable to the base; and
the airflow generator adapted to selectively deliver an airflow to the inlet of the electric vaporizer when the electric vaporizer is mounted to the base.

12. The device of claim 11, wherein the liquid vaporizable material includes at least one of a propylene glycol and a vegetable glycerin.

13. The device of claim 12, wherein the liquid vaporizable material further includes at least one of a lure scent, a cover scent, and a repellant scent.

14. The device of claim 12, wherein the liquid vaporizable material further includes a scent elimination material.

15. The device of claim 11, wherein the airflow generator can be turned on and turned off with a remote control.

16. The device of claim 11, wherein the base includes an adapter; a portion of the electric vaporizer being disposed in the adapter when the electric vaporizer is mounted to the base.

17. The device of claim 11, wherein the base defines a recess; the electric vaporizer being mountable to the base at the recess.

18. The device of claim 17, further comprising a collapsible bladder that carries the electric vaporizer; the collapsible bladder being seated in the recess when the electric vaporizer is mounted to the base.

19. The device of claim 11, wherein the electric vaporizer includes a sensor that energizes the burner when airflow is delivered to the electric vaporizer.

20. The device of claim 11, further comprising a timer that selectively powers the airflow generator.

21. The device of claim 11, further comprising a noise deadening insulation disposed adjacent the airflow generator.

22. An electric vaporizing device for creating and distributing a vapor at a location remote from a hunter to aid the hunt; the device comprising:
an electric vaporizer having an airflow inlet, a burner, a supply of liquid vaporizable material, an airflow channel, and an outlet;
the electric vaporizer having a first power source selectively connectable with the burner to energize the burner;
a base having a second power source and an airflow generator selectively powered by the second power source;
the base having an adapter tube;
the electric vaporizer being removably mountable to the base with a portion of the electric vaporizer disposed within the adapter tube; and
the airflow generator adapted to selectively deliver an airflow to the inlet of the electric vaporizer when the electric vaporizer is mounted to the base.

23. The device of claim 22, wherein the liquid vaporizable material includes at least one of a propylene glycol and a vegetable glycerin.

24. The device of claim 23, wherein the liquid vaporizable material further includes at least one of a lure scent, a cover scent, and a repellant scent.

25. The device of claim 23, wherein the liquid vaporizable material further includes a scent elimination material.

26. The device of claim 22, further comprising a collapsible bladder that carries the electric vaporizer.

27. The device of claim 26, wherein the bladder carries a valve; the adapter disposed through the valve when the electric vaporizer is mounted to the base.

28. The device of claim 22, wherein the electric vaporizer includes a sensor that energizes the burner when airflow is delivered to the electric vaporizer.

29. The device of claim 22, further comprising a timer that selectively powers the airflow generator.

* * * * *